(12) United States Patent
Yokouchi

(10) Patent No.: US 11,404,153 B2
(45) Date of Patent: Aug. 2, 2022

(54) DRUG INSPECTION ASSISTING APPARATUS AND DRUG INSPECTION ASSISTING METHOD

(71) Applicant: FUJIFILM Toyama Chemical Co., Ltd., Tokyo (JP)

(72) Inventor: Koji Yokouchi, Ashigarakami-gun (JP)

(73) Assignee: FUJIFILM Toyama Chemical Co., Ltd., Tokyo (JP)

( * ) Notice: Subject to any disclaimer, the term of this patent is extended or adjusted under 35 U.S.C. 154(b) by 334 days.

(21) Appl. No.: 16/662,216

(22) Filed: Oct. 24, 2019

(65) Prior Publication Data

US 2020/0058385 A1 Feb. 20, 2020

Related U.S. Application Data

(63) Continuation of application No. PCT/JP2018/016281, filed on Apr. 20, 2018.

(30) Foreign Application Priority Data

May 30, 2017 (JP) .............................. JP2017-106814

(51) Int. Cl.
*G16H 20/13* (2018.01)
*G06T 7/11* (2017.01)
*G06T 7/00* (2017.01)

(52) U.S. Cl.
CPC ............. *G16H 20/13* (2018.01); *G06T 7/001* (2013.01); *G06T 7/11* (2017.01)

(58) Field of Classification Search
CPC ........... G06T 7/001; G06T 7/11; G16H 20/13; G16H 30/00
See application file for complete search history.

(56) References Cited

U.S. PATENT DOCUMENTS 10,438,336 B2 * 10/2019 Takamori ............. G06K 9/4604
10,896,764 B2 * 1/2021 Yonaha .................. G16H 20/13
(Continued)

FOREIGN PATENT DOCUMENTS

CN    104173190 A    12/2014
CN    104582670 A    4/2015
(Continued)

OTHER PUBLICATIONS

Extended European Search Report for counterpart European Application No. 18810320.4, dated May 11, 2020.
(Continued)

*Primary Examiner* — Mia M Thomas
(74) *Attorney, Agent, or Firm* — Birch, Stewart, Kolasch & Birch, LLP

(57) ABSTRACT

According to an aspect of the present invention, a listing table is created for each kind of drug, and a single kind of drug among the drugs listed in the prescription is displayed on the display screen of the monitor. Therefore, mistakenly collated drugs can be found easily, and the pharmacist (user) can perform the drug inspection efficiently. In the present invention, the listing table for the drug similar to the single kind of drug may also be displayed on the display screen. The drug whose similarity to the single kind of drug is equal to or more than a threshold value may be determined as a similar drug, and the similar drug may be included in the listing table.

21 Claims, 22 Drawing Sheets

(56) References Cited

U.S. PATENT DOCUMENTS

| | | | | |
|---|---|---|---|---|
| 11,080,327 B2* | 8/2021 | Garcia | | G06V 20/20 |
| 2006/0058726 A1* | 3/2006 | Handfield | | G07F 11/44 |
| | | | | 221/9 |
| 2012/0200596 A1 | 8/2012 | Gotou et al. | | |
| 2013/0221082 A1* | 8/2013 | Botten | | G06F 16/5846 |
| | | | | 235/375 |
| 2013/0342676 A1* | 12/2013 | Amano | | B65B 57/10 |
| | | | | 348/86 |
| 2013/0343620 A1* | 12/2013 | Okuda | | G01F 23/02 |
| | | | | 382/128 |
| 2014/0318078 A1* | 10/2014 | Kondo | | G16H 20/13 |
| | | | | 382/141 |
| 2015/0170373 A1* | 6/2015 | Yonaha | | G06T 7/001 |
| | | | | 382/143 |
| 2015/0178674 A1 | 6/2015 | Yonaha et al. | | |
| 2016/0104277 A1* | 4/2016 | Takamori | | G01J 3/46 |
| | | | | 382/128 |
| 2016/0114925 A1 | 4/2016 | Yuyama et al. | | |
| 2016/0203291 A1* | 7/2016 | Ebata | | A61J 7/02 |
| | | | | 382/128 |
| 2016/0246928 A1* | 8/2016 | Rock | | G16H 20/10 |
| 2016/0364868 A1* | 12/2016 | Takahashi | | G01N 21/9508 |
| 2017/0305589 A1 | 10/2017 | Yuyama et al. | | |
| 2018/0174292 A1* | 6/2018 | Takamori | | G16H 20/10 |
| 2018/0247704 A1* | 8/2018 | Howieson | | A61J 7/04 |
| 2018/0366215 A1* | 12/2018 | Tribble | | G16H 20/13 |
| 2020/0035345 A1* | 1/2020 | Swarvar | | H04N 5/77 |
| 2021/0073986 A1* | 3/2021 | Kapur | | G06K 9/00147 |
| 2021/0074416 A1* | 3/2021 | Lantorno | | G16H 20/13 |
| 2021/0090704 A1* | 3/2021 | Poirier | | G06K 9/64 |

FOREIGN PATENT DOCUMENTS

| | | |
|---|---|---|
| CN | 105073082 A | 11/2015 |
| CN | 105307622 A | 2/2016 |
| JP | 2014-67342 A | 4/2014 |
| WO | WO 2016/047569 A1 | 3/2016 |

OTHER PUBLICATIONS

Chinese Office Action and Search Report for Chinese Application No. 201880029038.8, dated Mar. 30, 2021, with English translation.

Japanese Office Action dated Sep. 28, 2020 for Appiciation No. 2019-522021 with an English translation.

International Preliminary Report on Patentability, dated Dec. 12, 2019, and Written Opinion of the International Searching Authority, dated Jul. 17, 2018, for International Application No. PCT/JP2018/016281, with English translation.

International Search Report for International Application No. PCT/JP2018/016281, dated Jul. 17, 2018, with English translation.

* cited by examiner

FIG.8

| ATTRIBUTE INFORMATION | | MASTER IMAGE (FRONT) | MASTER IMAGE (BACK) |
|---|---|---|---|
| DRUG CODE | : XXX-XXXX | (A) iM1 | (○) iM2 |
| DRUG TYPE | : TABLET | | |
| SHAPE | : ROUND SHAPE | | |
| SIZE | : 10 mm IN DIAMETER | | |
| COLOR | : WHITE | | |
| MARK | : A | | |
| | | OK | |

| | | AFTER BREAKFAST | AFTER LUNCH | AFTER DINNER |
|---|---|---|---|---|
| L1A | 1ST DAY | BAG No. 1 (A) | BAG No. 2 (A) | BAG No. 3 (A) |
| | 2ND DAY | BAG No. 4 (A) | BAG No. 5 (A) | BAG No. 6 (A) |
| | 3RD DAY | BAG No. 7 (A) | BAG No. 8 (A) | BAG No. 9 (A) |
| | 4TH DAY | BAG No. 10 (A) | BAG No. 11 (A) | BAG No. 12 (A) |
| | 5TH DAY | BAG No. 13 (A) | BAG No. 14 (A) | BAG No. 15 (A) |
| | 6TH DAY | BAG No. 16 (A) | BAG No. 17 (A) | BAG No. 18 (A) |
| | 7TH DAY | BAG No. 19 (A) | BAG No. 20 (A) | BAG No. 21 (A) |

L1A: DRUG A MASTER IMAGE (A)

L1B: ATTRIBUTE INFORMATION
DRUG CODE : XXX-XXXX
DRUG TYPE : TABLET
SHAPE : ROUND SHAPE
SIZE : 10 mm IN DIAMETER
COLOR : WHITE
MARK : A

L1C

L1D: B1 ⇐ PREVIOUS DRUG | B3 [TO MENU] | B2 NEXT DRUG ⇒

FIG.10

| DRUG A MASTER IMAGE | | AFTER BREAKFAST | AFTER LUNCH | AFTER DINNER |
|---|---|---|---|---|
| (A) | 1ST DAY | BAG No. 1 (A)(A) | BAG No. 2 (A)(A) | BAG No. 3 (A)(A) |
| ATTRIBUTE INFORMATION<br>DRUG CODE : XXX-XXXX<br>DRUG TYPE : TABLET<br>SHAPE : ROUND SHAPE<br>SIZE : 10 mm IN DIAMETER<br>COLOR : WHITE<br>MARK : A | 2ND DAY | BAG No. 4 (A)(A) | BAG No. 5 (A)(A) | BAG No. 6 (A)(A) |
| | 3RD DAY | BAG No. 7 (A)(A) | BAG No. 8 (A)(A) | BAG No. 9 (A)(A) |
| | 4TH DAY | BAG No. 10 (A)(A) | BAG No. 11 (A)(A) | BAG No. 12 (A)(A) |
| | 5TH DAY | BAG No. 13 (A)(A) | BAG No. 14 (A)(A) | BAG No. 15 (A)(A) |
| | 6TH DAY | BAG No. 16 (A)(A) | BAG No. 17 (A)(A) | BAG No. 18 (A)(A) |
| | 7TH DAY | BAG No. 19 (A)(A) | BAG No. 20 (A)(A) | BAG No. 21 (A)(A) |
| | 8TH DAY | BAG No. 22 (A)(A) | BAG No. 23 (A)(A) | BAG No. 24 (A)(A) |
| | 9TH DAY | BAG No. 25 (A)(A) | BAG No. 26 (A)(A) | BAG No. 27 (A)(A) |
| | 10TH DAY | BAG No. 28 (A)(A) | BAG No. 29 (A)(A) | BAG No. 30 (A)(A) |
| | 11TH DAY | BAG No. 31 (A)(A) | BAG No. 32 (A)(A) | BAG No. 33 (A)(A) |
| | 12TH DAY | BAG No. 34 (A)(A) | BAG No. 35 (A)(A) | BAG No. 36 (A)(A) |
| | 13TH DAY | BAG No. 37 (A)(A) | BAG No. 38 (A)(A) | BAG No. 39 (A)(A) |
| | 14TH DAY | BAG No. 40 (A)(A) | BAG No. 41 (A)(A) | BAG No. 42 (A)(A) |

L2

← PREVIOUS DRUG | TO MENU | NEXT DRUG →

FIG.11

| DRUG A  MASTER IMAGE | | | | | | | | | |
|---|---|---|---|---|---|---|---|---|---|
| (A) | | | | | | | | | |
| ATTRIBUTE INFORMATION | | 1ST DAY | 2ND DAY | 3RD DAY | 4TH DAY | 5TH DAY | 6TH DAY | 7TH DAY | |
| DRUG CODE : XXX-XXXX | AFTER BREAKFAST | BAG No.1 (A) | BAG No.2 (A) | BAG No.3 (A) | BAG No.4 (A) | BAG No.5 (A) | BAG No.6 (A) | BAG No.7 (A) | |
| DRUG TYPE : TABLET | AFTER LUNCH | BAG No.8 (A) | BAG No.9 (A) | BAG No.10 (A) | BAG No.11 (A) | BAG No.12 (A) | BAG No.13 (A) | BAG No.14 (A) | 1ST WEEK |
| SHAPE : ROUND SHAPE | AFTER DINNER | BAG No.15 (A) | BAG No.16 (A) | BAG No.17 (A) | BAG No.18 (A) | BAG No.19 (A) | BAG No.20 (A) | BAG No.21 (A) | |
| SIZE : 10 mm IN DIAMETER | | 8TH DAY | 9TH DAY | 10TH DAY | 11TH DAY | 12TH DAY | 13TH DAY | 14TH DAY | |
| COLOR : WHITE | AFTER BREAKFAST | BAG No.22 (A) | BAG No.23 (A) | BAG No.24 (A) | BAG No.25 (A) | BAG No.26 (A) | BAG No.27 (A) | BAG No.28 (A) | |
| MARK : A | AFTER LUNCH | BAG No.29 (A) | BAG No.30 (A) | BAG No.31 (A) | BAG No.32 (A) | BAG No.33 (A) | BAG No.34 (A) | BAG No.35 (A) | 2ND WEEK |
| | AFTER DINNER | BAG No.36 (A) | BAG No.37 (A) | BAG No.38 (A) | BAG No.39 (A) | BAG No.40 (A) | BAG No.41 (A) | BAG No.42 (A) | |

⟵ PREVIOUS DRUG    [TO MENU]    NEXT DRUG ⟶

| DRUG B | MASTER IMAGE | | AFTER BREAKFAST | AFTER LUNCH | AFTER DINNER |
|---|---|---|---|---|---|
| | (B) | 1ST DAY | BAG No. 1 (B) | BAG No. 2 (B) | BAG No. 3 (B) |
| ATTRIBUTE INFORMATION | | 2ND DAY | BAG No. 4 (B) | BAG No. 5 (B) | BAG No. 6 (B) |
| DRUG CODE : YYY-YYYY | | 3RD DAY | BAG No. 7 (B) | BAG No. 8 (B) | BAG No. 9 (B) |
| DRUG TYPE : TABLET | | 4TH DAY | BAG No. 10 (B) | BAG No. 11 (B) | BAG No. 12 (B) |
| SHAPE : ROUND SHAPE | | 5TH DAY | BAG No. 13 (B) | BAG No. 14 (B) | BAG No. 15 (B) |
| SIZE : 7 mm IN DIAMETER | | 6TH DAY | BAG No. 16 (B) | BAG No. 17 (B) | BAG No. 18 (B) |
| COLOR : WHITE | | 7TH DAY | BAG No. 19 (B) | BAG No. 20 (B) | BAG No. 21 (B) |
| MARK : B | | | | | |

L6

⟨PREVIOUS DRUG    TO MENU    NEXT DRUG⟩

FIG.17

| DRUG A MASTER IMAGE | | AFTER BREAKFAST | AFTER LUNCH | AFTER DINNER |
|---|---|---|---|---|
| (A) | 1ST DAY | BAG No. 1 (A) | BAG No. 2 (A) | BAG No. 3 (A) |
| | 2ND DAY | BAG No. 4 (A) | BAG No. 5 (A) | BAG No. 6 (A) |
| ATTRIBUTE INFORMATION | 3RD DAY | BAG No. 7 (A) | BAG No. 8 (A) | BAG No. 9 (A) |
| DRUG CODE : XX-XXXX | 4TH DAY | BAG No. 10 (A) | BAG No. 11 (A) | BAG No. 12 (A) |
| DRUG TYPE : TABLET | 5TH DAY | BAG No. 13 (A) | BAG No. 14 (A) | BAG No. 15 (A) |
| SHAPE : ROUND SHAPE | 6TH DAY | BAG No. 16 (A) | BAG No. 17 (A) | BAG No. 18 (A) |
| SIZE : 10 mm IN DIAMETER | 7TH DAY | BAG No. 19 (A) | BAG No. 20 (A) | BAG No. 21 (A) |
| COLOR : WHITE | | | | |
| MARK : A | | | | |

◁ PREVIOUS DRUG     TO MENU     NEXT DRUG ▷

|  | DRUG A | DRUG B | DRUG C | DRUG D |
|---|---|---|---|---|
| DRUG A | 1.0 | 0.6 | 0.5 | 0.7 |
| DRUG B | 0.6 | 1.0 | 0.5 | 0.8 |
| DRUG C | 0.5 | 0.5 | 1.0 | 0.5 |
| DRUG D | 0.7 | 0.8 | 0.5 | 1.0 |

|  | DRUG A | DRUG B | DRUG C | DRUG D |
|---|---|---|---|---|
| DRUG A | SAME | DISSIMILAR | DISSIMILAR | DISSIMILAR |
| DRUG B | DISSIMILAR | SAME | DISSIMILAR | SIMILAR |
| DRUG C | DISSIMILAR | DISSIMILAR | SAME | DISSIMILAR |
| DRUG D | DISSIMILAR | SIMILAR | DISSIMILAR | SAME |

FIG.24

|  | SIMILAR DRUG |
|---|---|
| DRUG A | NONE |
| DRUG B | DRUG D |
| DRUG C | NONE |
| DRUG D | DRUG B |

DRUG INSPECTION ASSISTING APPARATUS AND DRUG INSPECTION ASSISTING METHOD

CROSS-REFERENCE TO RELATED APPLICATIONS

The present application is a Continuation of PCT International Application No. PCT/JP2018/016281 filed on Apr. 20, 2018 claiming priority under 35 U.S.C. § 119(a) to Japanese Patent Application No. 2017-106814 filed on May 30, 2017. Each of the above applications is hereby expressly incorporated by reference, in its entirety, into the present application.

BACKGROUND OF THE INVENTION

1. Field of the Invention

The present invention relates to a drug inspection assisting apparatus and a drug inspection assisting method and, more specifically, to a drug inspection assisting apparatus and a drug inspection assisting method which assist inspection to check whether or not drugs packaged in a packaging bag are drugs exactly according to a prescription.

2. Description of the Related Art

In medical settings, commonly, a patient brings a prescription written by a medical doctor to a pharmacy and drugs are dispensed according to the prescription in the pharmacy. When dispensing, so-called "one dose packaging" is often performed to package the prescribed drugs in a packaging bag for each dose. This packaging of drugs (one dose packaging) is expected to achieve effects such as prevention of forgetting to take drugs, facilitation of taking drugs, or facilitation of management of drug administration.

In the meantime, when a pharmacist dispenses or provides drugs, it is requested to check the prescribed contents based on listed items in the prescription, patient information, and the like. Because the pharmacist is required to confirm directions for each dose in inspections of the packaged drugs, the pharmacist bears large burden in the inspections. In order to lighten the burden on the pharmacist in inspections, an inspection assisting method and an inspection assisting apparatus have been developed in order to collate the contents written in a prescription regarding the kinds, quantity, and the like of drugs with the contents in packaged drugs. For example, Japanese Patent Application Laid-Open No. 2014-067342 (hereinafter referred to as "PTL 1") discloses a technology to collate drug master images with captured images to identify which drugs are present in the captured images, and to create a listing table that displays the drug master images and drug area images showing each drug identified in the captured images while their positions aligned with each other. According to PTL 1, it is possible to facilitate collation of the captured images with the master images by the listing table, and improve efficiency in visual inspections by the pharmacist.

CITATION LIST

PTL 1: Japanese Patent Application Laid-Open No. 2014-067342

SUMMARY OF THE INVENTION

In PTL 1, the listing table including the master image and the captured images is created. Because the listing table displays the captured images for all kinds of drugs listed in the prescription, images of different drugs are displayed adjacent to each other in the vertical and/or lateral directions. Therefore, it is difficult to understand whether the listing shows a collation result for other drugs or a collation error occurs, thereby requiring time and effort for inspections.

The present invention is made in view of such circumstances, and the present invention aims to provide a drug inspection assisting apparatus and a drug inspection assisting method which enable pharmacist to effectively perform drug inspection work.

In order to achieve the foregoing object, according to a first aspect of the present invention, a drug inspection assisting apparatus for inspecting drugs dispensed and packaged in a packaging bag according to a prescription, includes: a drug collating unit configured to collate a reference image of each drug listed in the prescription and a collation-target image based on a captured image of drugs packaged in the packaging bag and determine whether or not the drug shown by the collation-target image and the drug shown by the reference image are the same drug; a listing-table creating unit configured to create, for each kind of the drugs to be packaged in the packaging bag, a listing table including the reference image of drug to be dispensed according to the prescription and all images which are determined to show the same drug as the drug shown by the reference image, among collation-target images; and a display control unit configured to cause a display device to display the listing table for a single kind of drug among kinds of the drugs listed in the prescription on a display screen.

With the first aspect, the listing table is created for each kind and the listing table for a single kind of drug among the drugs listed in the prescription is displayed on the display screen of the display device. Therefore, mistakenly collated drugs can be found easily, and the pharmacist (user) can perform the drug inspection efficiently.

According to a second aspect, in the drug inspection assisting apparatus, the display control unit causes the display device to display the listing table for a similar drug which is similar to the single kind of drug on the display screen. With the second aspect, the listing table for the similar drug is also displayed so that the pharmacist can easily recognize a collation error even when the images are switched between similar drugs which are mistakenly determined.

According to a third aspect, the drug inspection assisting apparatus of the second aspect further includes a similarity calculating unit configured to calculate similarity between the drugs, in which the display control unit determines the drug whose calculated similarity to the single kind of drug is equal to or more than a threshold value as the similar drug, and causes the display device to display the listing table for the similar drug. The third aspect defines an example of a specific manner to determine the similar drugs.

According to a fourth aspect, in the drug inspection assisting apparatus of the second or third aspect, the display control unit causes the display device to display, according to an instruction to display a designated kind of drug, the listing table for the designated kind of drug and the similar drug on the display screen. With the fourth aspect, the listing table including the similar drug to a desired kind is displayed on the display screen, so that the pharmacist can perform inspection efficiently.

According to a fifth aspect, in the drug inspection assisting apparatus of any one of the first to fourth aspects, the listing-table creating unit creates the listing table including inspection assisting information of the collation-target images, and the display control unit causes the display device to display the listing table including the inspection assisting information on the display screen. With the fifth aspect, the listing table including the inspection assisting information is displayed on the display screen, so that the pharmacist can perform the inspection more efficiently. Note that the inspection assisting information in the fifth aspect is information for efficiently performing collation and inspection of the drugs, and may include dosing day (indicating a day for which the packaging bag is prepared), dosing timing, packaging bag number, and the like about the drugs shown by the collation-target images included in the listing table.

According to a sixth aspect, in drug inspection assisting apparatus of the fifth aspect, the listing-table creating unit changes an amount of the inspection assisting information to be included in the listing table depending on a number of the collation-target images included in the listing table. As in the sixth aspect, instead of fixing the amount of the inspection assisting information, the amount of the inspection assisting information included in the listing table is changed depending on the number of collation-target images (for example, through decreasing the amount of the inspection assisting information when the number of collation-target images is increased). Therefore, even when there are a large number of drugs, it becomes easier to view the listing table (images of drugs) so that the pharmacist can perform the inspection efficiently.

According to a seventh aspect, in the drug inspection assisting apparatus of the fifth or sixth aspect, the display control unit causes the display device to display the inspection assisting information regarding only a designated image among the collation-target images displayed on the display screen. As in the seventh aspect, even when there are a large number of collation-target images (number of drugs) and less inspection assisting information to be displayed, the inspection assisting information about the designate image is displayed. Therefore, it is possible to check the necessary inspection assisting information so that the pharmacist can perform the inspection efficiently. Note that the inspection assisting information displayed in the seventh aspect may be displayed on a different screen from that of the listing table.

According to an eighth aspect, in the drug inspection assisting apparatus of any one of the first to seventh aspects, the reference image includes a plurality of images obtained by imaging each of the drugs to be dispensed according to the prescription from a plurality of directions; and the listing-table creating unit creates the listing table including the plurality of images.

According to a ninth aspect, the drug inspection assisting apparatus of any one of the first to eighth aspects includes an imaging unit configured to image the packaged drugs from a plurality of directions to obtain a plurality of captured images, in which the listing-table creating unit creates the listing table including a plurality of the collation-target images respectively corresponding to the plurality of captured images. The drugs may face in various directions in the packaging bag (facing the front direction, back direction, or the like). The images captured from a plurality of directions are included in the listing table as in the ninth aspect so that collation can be performed securely and the pharmacist can perform the inspection efficiently.

According to a tenth aspect, in the drug inspection assisting apparatus of any one of the first to ninth aspects, the listing-table creating unit creates the listing table with a size of the collation-target image adjusted to the reference image by magnifying or reducing the collation-target image. By marching sizes of the collation-target image to the reference image each other as in the tenth aspect, the listing table can be easily viewed and the pharmacist can perform the inspection efficiently.

According to an eleventh aspect, in the drug inspection assisting apparatus of any one of the first to tenth aspects, the listing-table creating unit creates the listing table with a direction of the collation-target image adjusted to the reference image by rotating the collation-target image. By matching the directions of the reference image and the collation-target images each other as in the eleventh aspect, the listing table can be easily viewed and the pharmacist can perform the inspection efficiently.

According to a twelfth aspect, in the drug inspection assisting apparatus of any one of the first to eleventh aspects, the reference image is a master image stored in advance for each drug possible to be dispensed or a processed master image obtained by performing image-processing on the master image. Through performing the image processing on the master image as necessary as in the twelfth aspect, visual confirmation and collation of the drugs can be performed easily.

According to a thirteenth aspect, in the drug inspection assisting apparatus of any one of the first to twelfth aspects, the collation-target image is the captured image or a processed captured image obtained by performing image-processing on the captured image. Through performing the image processing on the captured image as necessary as in the thirteenth aspect, visual confirmation and collation of the drugs can be performed easily.

According to a fourteenth aspect, in the drug inspection assisting apparatus of the thirteenth aspect, the image processing is an image-processing for extracting a drug region from the captured image. For example, when a plurality of drugs are included in the captured image or regions other than the drugs are also imaged in the captured image, by extracting the drug region as in the fourteenth aspect, collation and inspection can be performed efficiently.

According to a fifteenth aspect, the drug inspection assisting apparatus of any one of the first to fourteenth aspects includes a drug selecting unit configured to receive selection of a drug from a user, in which the display control unit causes the display device to display the listing table for the drug for which the selection is received. With the fifteenth aspect, the user (pharmacist) can display the listing table for a desired drug.

According to a sixteenth aspect, in the drug inspection assisting apparatus of any one of the first to fifteenth aspects, the display control unit causes the display device to display the listing table on a single display screen. With the sixteenth aspect, the listing table is displayed on a single screen, so that scrolling of the screen is unnecessary and checking of the collation result can be performed easily even when there are a large number of packaging bags. Note that the listing table can be displayed on a single screen by reducing the size of the images of the drugs, setting the resolution of display to be equal to or less than the resolution of the display screen, or the like.

In order to achieve the foregoing object, according to a seventeenth aspect of the present invention, a drug inspection assisting method for inspecting drugs dispensed and packaged in packaging bag according to a prescription by a drug inspection assisting apparatus, includes: by the drug inspection assisting apparatus, performing a drug collating step of collating a reference image of each drug listed in the prescription and a collation-target image based on a captured image of drugs packaged in the packaging bag to determine whether or not the drug shown by the collation-target image and the drug shown by the reference image are the same drug; by the drug inspection assisting apparatus, performing a listing-table creating step of creating, for each kind of the drugs to be packaged in the packaging bag, a listing table including the reference image of drug to be dispensed according to the prescription and all images which are determined to show the same drug as the drug shown by the reference image, among collation-target images; and by the drug inspection assisting apparatus, performing a display control step of causing a display device to display the listing table for a single kind of drug among kinds of the drugs listed in the prescription on a display screen.

According to an eighteenth aspect, in the drug inspection assisting method of the seventeenth aspect, the display device is caused to display the listing table for a similar drug which is similar to the single kind of drug on the display screen in the display control step by the drug inspection assisting apparatus. With the eighteenth aspect, the pharmacist can easily recognize the collation error even when images are switched between similar drugs which are mistakenly determined, as in the case of the second aspect.

According to a nineteenth aspect, the drug inspection assisting method of the eighteenth aspect further includes a similarity calculating step of calculating similarity between the drugs by the drug inspection assisting apparatus, and it is determined that a drug whose calculated similarity to the single kind of drug is equal to or more than a threshold value as the similar drug, and the display device is caused to display the listing table for the similar drug by the drug inspection assisting apparatus. The nineteenth aspect defines an example of a specific manner to determine the similar drugs as in the case of the third aspect.

According to a twentieth aspect, in the drug inspection assisting method of the eighteenth or nineteenth aspect, in the display control step, according to an instruction to display a designated kind, the listing table for the designated kind of drug and the similar drug is displayed on the display screen. With the twentieth aspect, the pharmacist can perform the inspection efficiently as in the case of the fourth aspect.

Assisting method according to a twenty-first aspect, in the drug inspection assisting method of any one of the seventeenth to twentieth aspects, in the display control step, the listing table is displayed on a single display screen of the display device. With the twenty-first aspect, checking of the collation result can be performed easily as in the case of the sixteenth aspect.

As described above, with the drug inspection assisting apparatus and the drug inspection assisting method according to the present invention, pharmacists can perform the drug inspection work efficiently.

BRIEF DESCRIPTION OF THE DRAWINGS

FIG. 8 is a diagram showing master images and attribute information of a drug.

FIG. 9 is a diagram showing a state where the first listing table is displayed.

FIG. 10 is another diagram showing a state where the first listing table is displayed.

FIG. 11 is a diagram showing a state where the first listing table in a different format is displayed.

FIG. 12 is a diagram showing a state where the first listing table is displayed with inspection assisting information omitted.

FIG. 16 is a diagram showing a state where images of front side and back side of drugs are displayed on the first listing table.

FIG. 17 is a diagram showing a state where the first listing table is scrolled and displayed.

FIG. 24 is a diagram showing a table of similar drugs.

DESCRIPTION OF THE PREFERRED EMBODIMENTS

Hereinafter, an embodiment of a drug inspection assisting apparatus and a drug inspection assisting method according to the present invention is to be described in details by referring to the accompanying drawings.

First Embodiment

Figure 1:
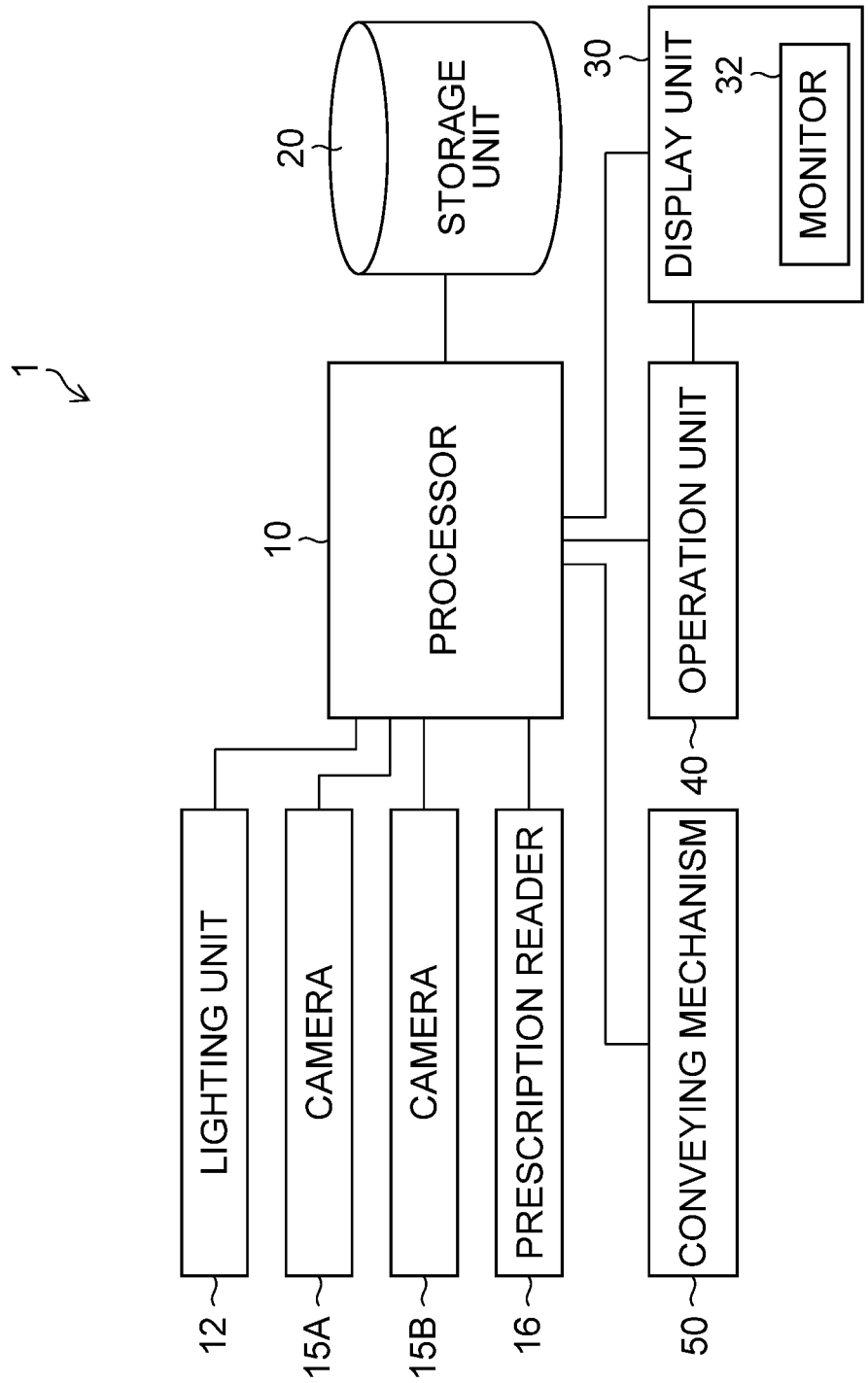
FIG. 1 is a block diagram showing a configuration of a drug inspection assisting apparatus according to an embodiment of the present invention.

FIG. 1 is a diagram showing a configuration of a drug inspection assisting apparatus 1 according to an embodiment of the present invention. The drug inspection assisting apparatus 1 includes a processor 10, a storage unit 20, a display unit 30, an operation unit 40, and a conveying mechanism 50. To the processor 10, a lighting unit 12, a camera 15A, a camera 15B, and a prescription reader 16 are connected.

Figure 2:
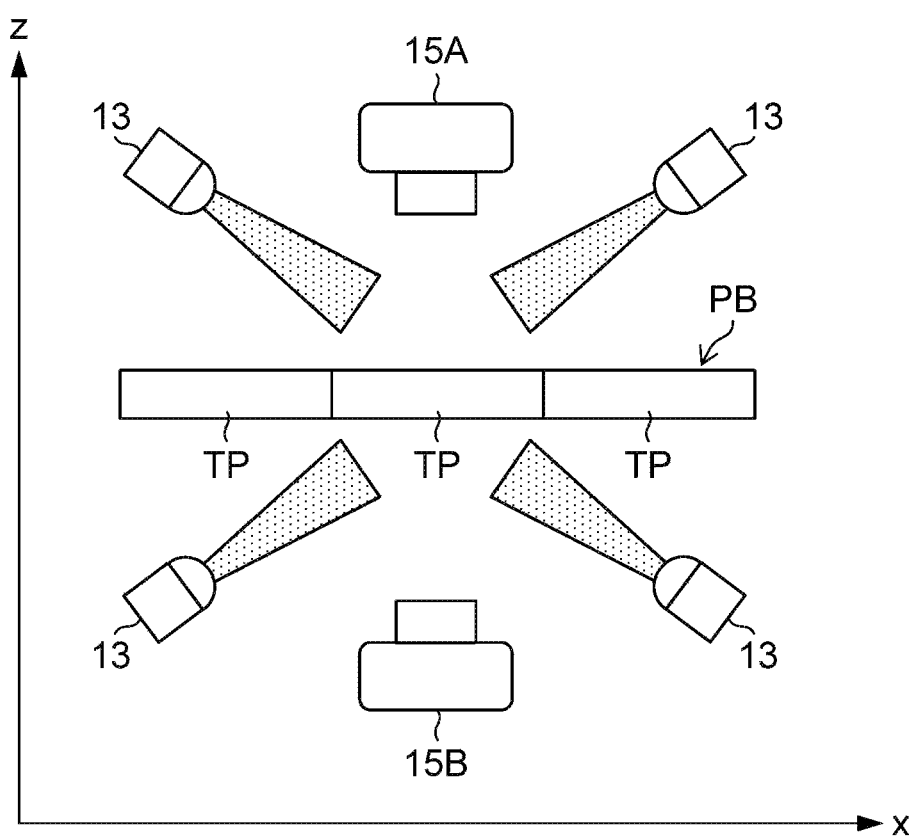
FIG. 2 is a diagram showing a state when obtaining an image of a packaging bag under lighting.
Figure 3:
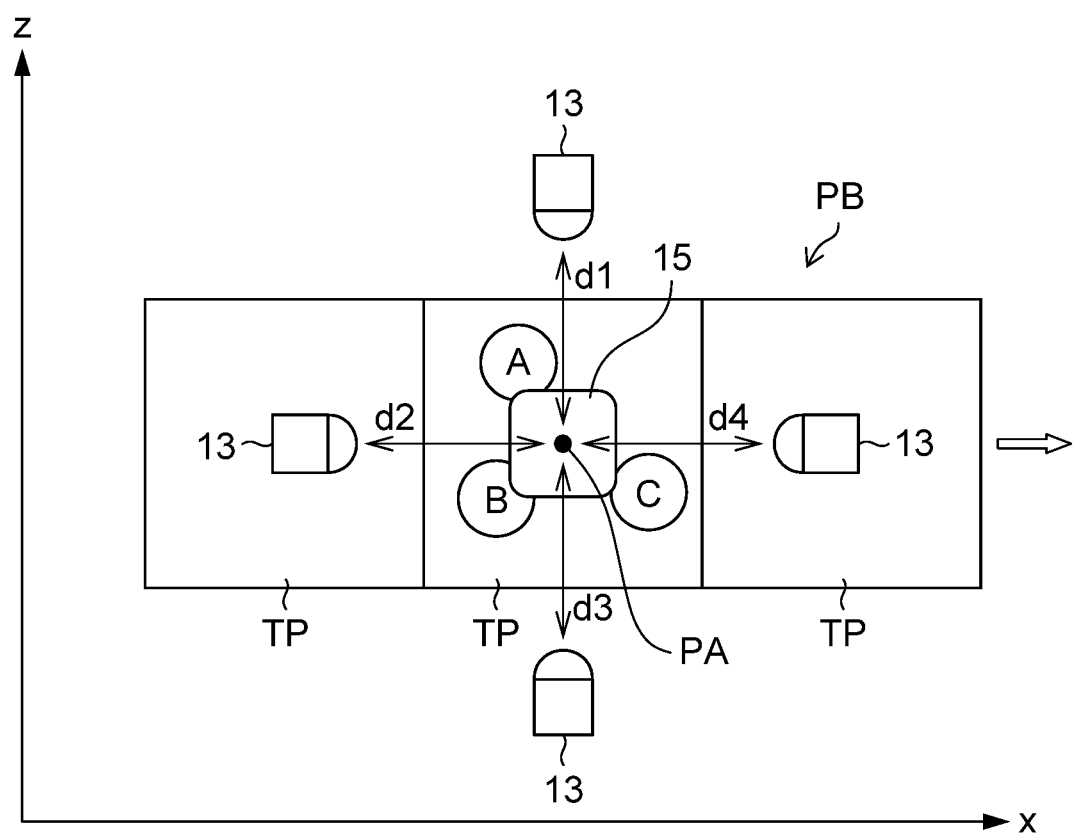
FIG. 3 is another diagram showing a state when an image of a packaging bag is obtained under lighting.

The camera 15A and the camera 15B are configured with digital cameras. As shown in FIG. 2, the camera 15A is disposed on an upper side (+Z-side in FIG. 2) of a strip package PB which includes packaging bags TP (drug pack) formed in series, and the camera 15B is disposed on a lower side (−Z-side in FIG. 2) of the strip package PB to capture images of the drugs packaged in packaging bags TP from above and below (a plurality of different directions). The packaging bags TP (strip package PB) are conveyed by the conveying mechanism 50 in +X-direction in FIG. 2 (axis along the longitudinal direction of the strip package PB; a direction shown by an arrow in FIG. 2), and a plurality of light sources 13 provided to the lighting unit 12 illuminate the packaging bags TP from four directions when capturing an image of the packaging bags TP. In FIG. 3, distances (d1, d2, d3, and d4) between each of the plurality of light sources 13 and an imaging optical axis PA of the cameras 15A, 15B are the same. That is, the plurality of light sources 13 are disposed at equivalent intervals (d1=d2=d3=d4) from the imaging optical axis PA.

The prescription reader 16 reads out prescription information. For example, the prescription reader 16 reads information such as a name of patient, prescribed drugs, doses thereof, and the like from the prescription written on paper by OCR (Optical Character Recognition). When a barcode or the like showing the information regarding the prescribed drugs is recorded on the prescription, the information such as the prescribed drugs, doses thereof, and the like may be read out from the barcode. Further, a user may read out the prescription and input the prescription information through an input device such as a keyboard provided to the operation unit 40.

<Configuration of Processor>

Figure 4:
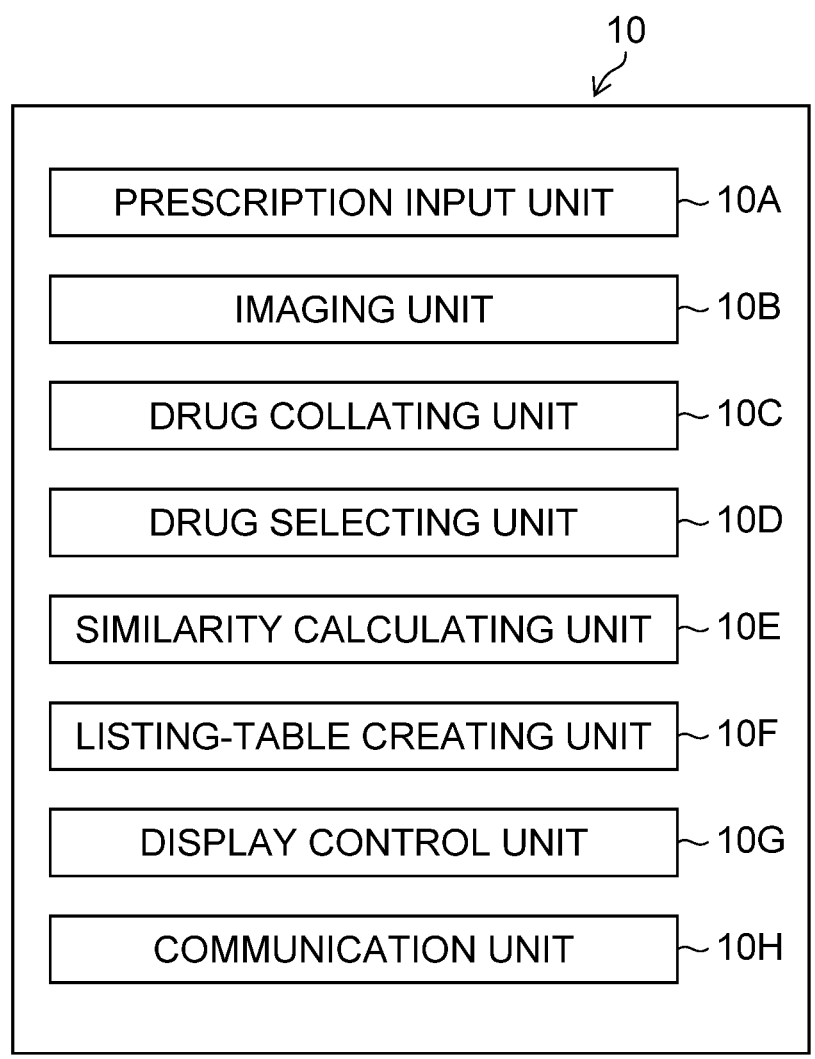
FIG. 4 is a diagram showing a functional configuration of a processor.

FIG. 4 is a diagram showing a functional configuration of the processor 10. The processor 10 includes a prescription input unit 10A, an imaging unit 10B (imaging unit), a drug collating unit 10C (drug collating unit), a drug selecting unit 10D (drug selecting unit), a similarity calculating unit 10E (similarity calculating unit), a listing-table creating unit 10F, a display control unit 10G (display control unit), and a communication unit 10H. The functions of these units may be achieved with a CPU (Central Processing Unit) and devices such as various kinds of electronic circuits through referring to data stored in an EEPROM (Electronically Erasable and Programmable Read Only Memory: non-transitory recording medium) and the like. Further, those functions are performed by executing a drug inspection assisting program stored in a ROM (Read Only Memory: non-transitory recording medium) and the like. When performing processes, a RAM (Random Access Memory) and the like are used as a temporary storage area and a work area. Note that illustrations of those devices are omitted in FIG. 4.

The prescription input unit 10A controls the prescription reader 16 to read out the information written in the prescription. The imaging unit 10B controls the camera 15A and the camera 15B to capture images of drugs packaged in a packaging bag TP. The drug collating unit 10C determines whether or not a drug shown in a collation-target image (image to be collated) and a drug shown in a reference image are the same drug. The drug selecting unit 10D receives selection of a drug from the user via the operation unit 40. The similarity calculating unit 10E calculates similarity between drugs (for example, between the collation-target image and the reference image). The listing-table creating unit 10F (listing-table creating unit) creates a listing table. Inspection assisting information is included in the listing table according to the collation-target image. The display control unit 10G performs display control of the listing table, the inspection assisting information, and the like. The communication unit 10H communicates with a server, a database, and the like, not shown, via a network to obtain master images of drugs, attribution information thereof, and the like. Detailed processes of the drug inspection assisting method performed by those functions are to be described later.

The functions of the processor 10 can be achieved by using various kinds of processors (processors). The various kinds of processors may include, for example, a CPU (Central Processing Unit) that is a general-purpose processor capable of executing software (program) and achieving various kinds of functions. Further, the various kinds of processors may include a programmable logic device (PLD) such as an FPGA (Field Programmable Gate Array) and the like that is a processor capable of changing circuit configuration after being manufactured. Further, the various kinds of processors may include a dedicated electric circuit such as an ASIC (Application Specific Integrated Circuit) or the like that a processor having a circuit configuration designed specially for performing specific processes.

The functions of each unit may be achieved by a single processor or may be achieved by combining a plurality of processors. Also, a plurality of functions may be achieved by a single processor. As an example of a case configuring a plurality of functions with a single processor, first, there is a mode, as is represented by a computer such as a client and a server, in which a single processor is configured with a combination of one or more CPUs and software, and the processor achieves a plurality of functions. Secondly, there is a mode represented by a system on chip (System On Chip: SoC) employing a processor which achieves functions of the entire system with a single IC (Integrated Circuit) chip. As described above, the various kinds of functions may be configured as hardware configuration by using one or more of the various kinds of processors described above. Further, for operating those processors, computer-readable codes of a program for causing the drug inspection assisting apparatus to perform the drug inspection assisting method according to the present invention are recorded in a non-transitory recording medium (not shown) such as a ROM (Read Only Memory).

<Configuration of Storage Unit>

Figure 5:
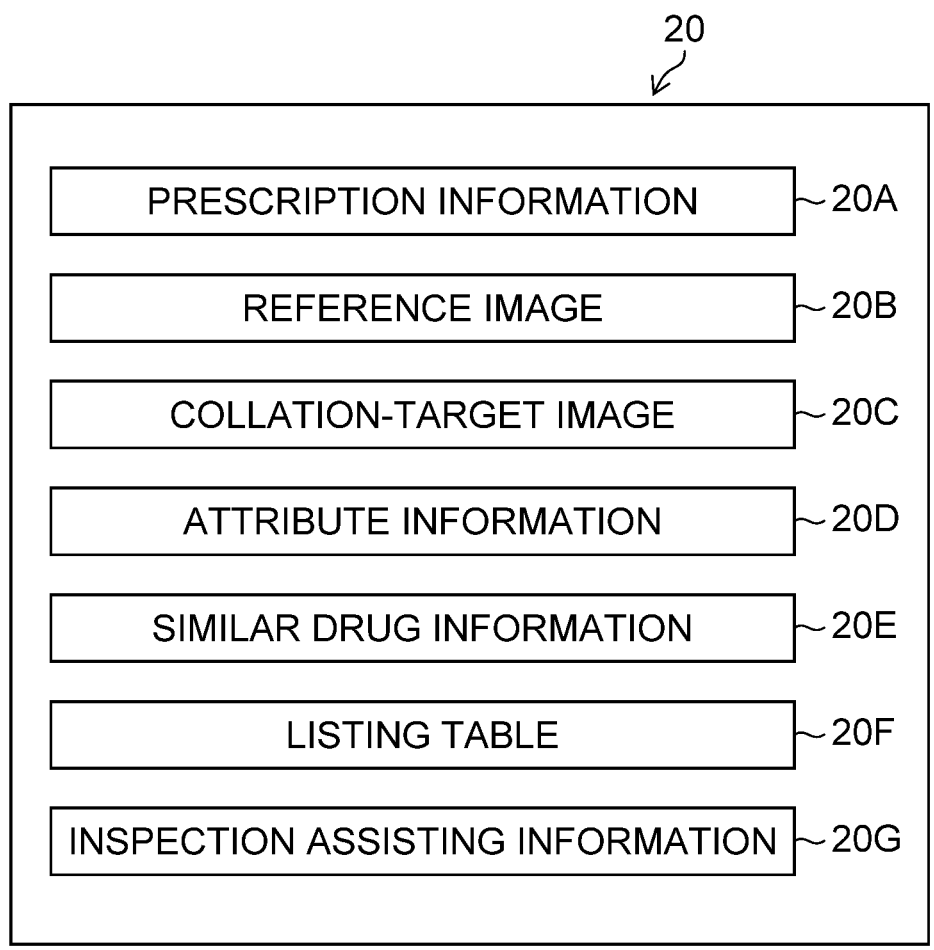
FIG. 5 is a diagram showing information stored in a storage unit.

The storage unit 20 is configured with a non-transitory recording medium such as a CD (Compact Disk), a DVD (Digital Versatile Disk), a hard disk (Hard Disk), and a various kinds of semiconductor memories, and stores the images and information shown in FIG. 5 with associating (relating) them with each other. Prescription information 20A is the information read out via the prescription reader 16. The prescription information 20A includes a name of patient, and identification information, doses, directions and the like of each drug. A reference image 20B is a master image of each drug which is stored in advance, or a processed master image which is obtained by image-processing the master image. That is, the master image or the processed master image is stored as the reference image. A collation-target image 20C is a captured image imaged by the imaging unit 10B and cameras 15A, 15B or a processed captured image (image based on the captured image) obtained by image-processing the captured image. That is, the captured image or the processed captured image is stored as the collation-target image. Attribute information 20D may be drug type, shape, size, color, mark, and the like of each drug, but not limited to those. Similar drug information 20E is information indicating similar drugs for a certain drug. A listing table 20F is information showing a listing table of a collation result created by the processor 10 (listing-table creating unit 10F). Inspection assisting information 20G (inspection assisting information) is information for efficiently performing collation and inspection of drugs. The inspection assisting information 20G can include dosing date (indicating the day for which the packaging bag is prepared), dosing timing, packaging bag number, and the like regarding drugs shown in the collation-target images included in the listing table. When performing processes by the processor 10, those images and information are read and written between the processor 10 and the storage unit 20.

<Configurations of Display Unit and Operation Unit>

The display unit 30 (display device) includes a monitor 32 (display device), and is capable of displaying the prescription information read out via the prescription reader 16, images of the packaged drugs, information and images stored in the storage unit 20, listing tables, inspection assisting information, and the like. The operation unit 40 includes a pointing device such as a mouse and an input device such as a keyboard. The user can operate the images, buttons, and the like displayed on the monitor 32 with the operation unit 40.

<Processes of Drug Inspection Assisting Method>
<Creation of Listing Table>

Figure 6:
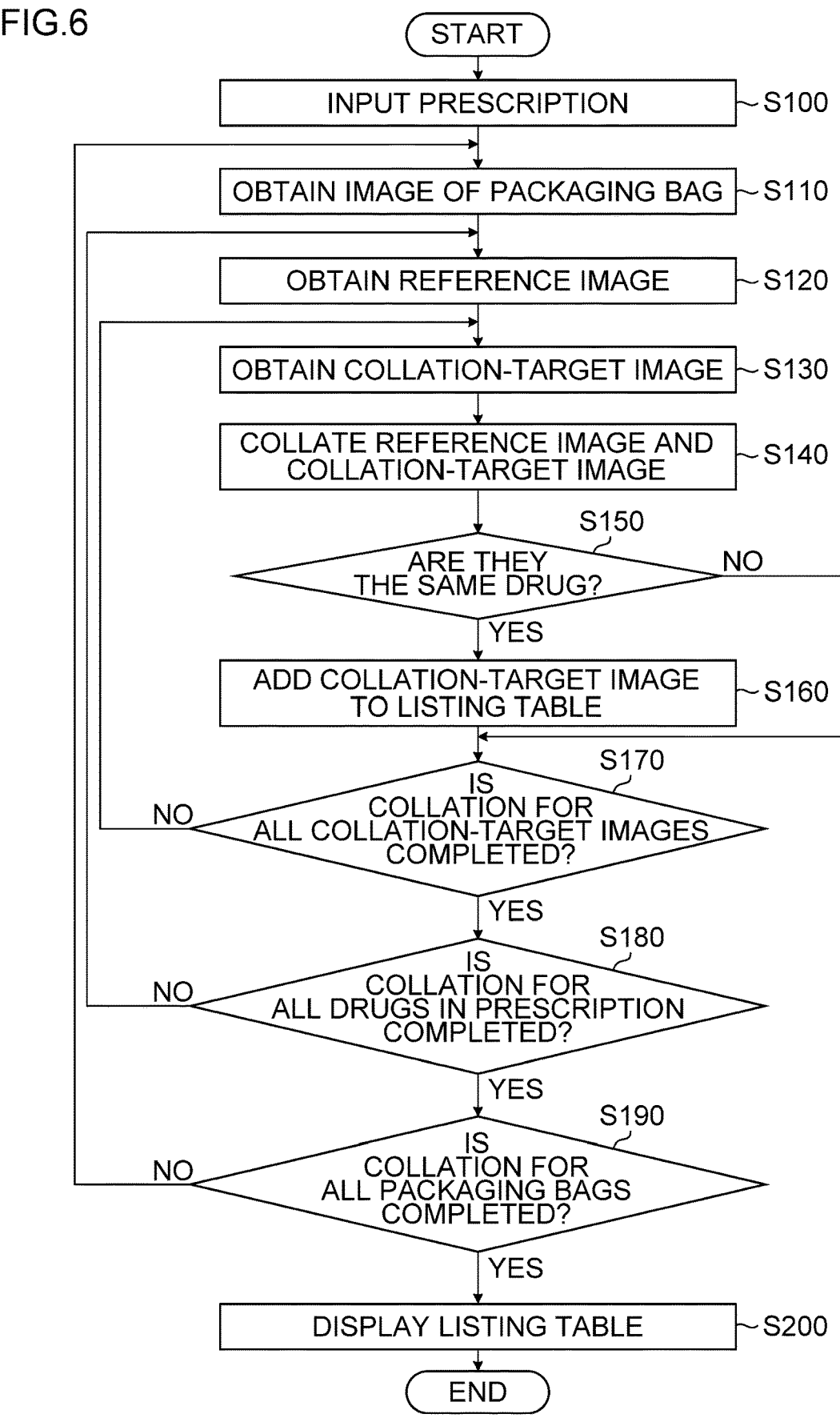
FIG. 6 is a flowchart showing processes for creating and displaying a first listing table.

The processes (creation and display of the listing table) of the drug inspection assisting method by the drug inspection assisting apparatus 1 having the configuration described above is described. FIG. 6 is a flowchart showing the processes of the drug inspection assisting method.

In step S100, the prescription information is read out by the prescription reader 16 and the processor 10 (prescription input unit 10A). Alternatively, the prescription information 20A previously stored in the storage unit 20 may be read out. Hereinafter, explanations are provided assuming that the contents of the prescription are "Take two tablets of drug A and one tablet each of drugs B, C, and D in each dose, To be taken three times a day after meals" (a plurality of drugs are listed in the prescription).

Figure 7A:
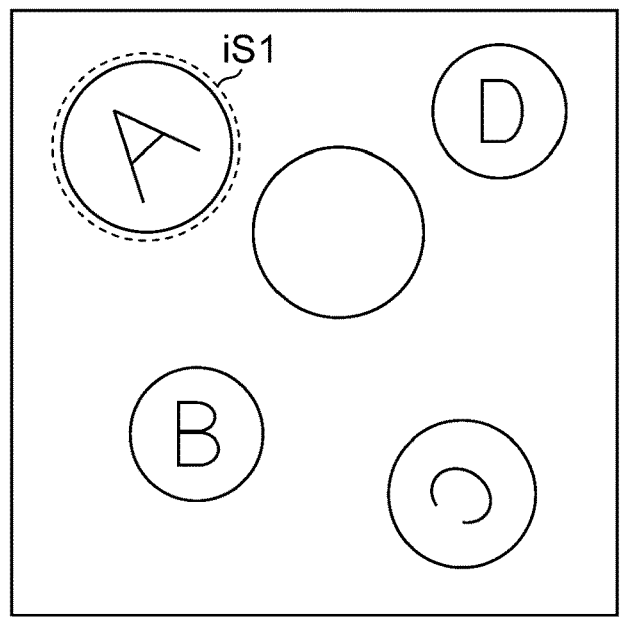
FIG. 7A is a diagram showing an image obtained by imaging a packaging bag from an upper direction and a lower direction.
Figure 7B:
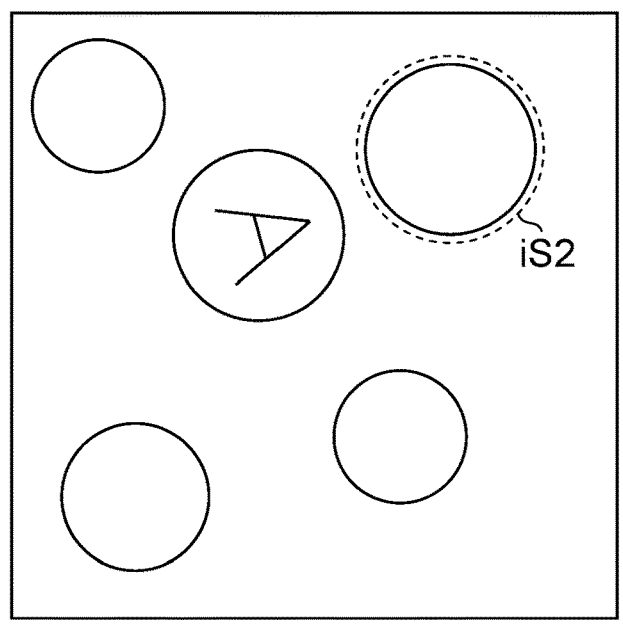
FIG. 7B is a diagram showing an image obtained by imaging a packaging bag from an upper direction and a lower direction.

In step S110, the imaging unit 10B images the drugs packaged in the packaging bag TP of the strip package PB from a plurality of directions (upper and lower directions) by controlling the cameras 15A, 15B to obtain a plurality of captured images. FIG. 7A is an image of the packaging bag TP imaged from the upper direction, and FIG. 7B part is an image of the same packaging bag imaged from the lower direction. All drugs do not necessarily face in the same direction (front/back and rotating degrees within a plane) in the packaging bag TP. The drugs may face different directions from each other as shown in FIG. 7A and FIG. 7B. The processor 10 (drug collating unit 10C) associates ID (identification) which identifies the packaging bag with the images of the packaging bag TP.

In step S120, reference images are obtained for the drugs included in the prescription information read out in step S100. The master images stored in the storage unit 20 may directly be obtained and used as the reference images. Alternatively, the master images are subject to image-processing such as magnification or reduction, brightness adjustment, and the like and then used as the reference images. FIG. 8 is an example of the reference image, showing the master image as the reference image of the drug A that is to be dispensed according to the prescription. In the example of FIG. 8, the master images include a plurality of images (master images iM1, iM2) obtained by imaging the drug from different directions (upper and lower directions of the drug A). The master image iM1 is the image of the front surface of the drug A, while the master image iM2 is the image of the back surface of the drug A.

Further, in the example of FIG. 8, the attribute information 20D indicating attribute of the drug A is associated with the master images iM1, iM2, and the processor 10 (display control unit 10G) displays the master images (or reference images) and the attribute information on the monitor 32 according to an operation of the user via the operation unit 40.

In step S130, drug regions of each drug are extracted from the captured images, and subject to image-processing such as magnification, reduction, and brightness adjustment is performed as necessary. The same processing is performed on the other drugs. Then, the images of the extracted drug regions or images (processed captured images) after image-processing the images of the extracted drug regions, are obtained as the collation-target images. In the example of FIG. 7A and FIG. 7B, collation-target images iS1 and iS2 (a plurality of collation-target images corresponding to a plurality of captured images, respectively) for the drug A are obtained. The collation-target image iS1 is the image of the front surface of the drug A, and the collation-target image iS2 is the image of the back surface of the drug A. The processor 10 (drug collating unit 10C) associates the ID for identifying the drug with the collation-target images. Note that the collation-target images may not necessarily be obtained from the captured images as described above. The collation-target images 20C previously stored in the storage unit 20 may be read out.

After obtaining the reference images and the collation-target images, the processor 10 (drug collating unit 10C) collates the reference images with the collation-target images (step S140: drug collating step), and determines whether or not the drug shown in the collation-target images and the drug shown in the reference images are the same drug (step S150: drug collating step). When it is determined that they are the same drug, the processor 10 (listing-table creating unit 10F) adds the collation-target images to the listing table (step S160: listing table creating step), and proceeds to step S170. Note that collation of the reference image with the collation-target image can be performed by determining whether or not a template set in the reference image matches a region of interest set in the collation-target region (template matching), or whether or not local feature amounts of the reference image and the collation-target image match each other, for example. Further, the collation-target image may be magnified or reduced in size, rotated, and the like to align the direction thereof with the reference image when performing collation.

In the example shown in FIG. 7A, FIG. 7B, and FIG. 8, the processor 10 (drug collating unit 10C) determines that "the drug shown in the collation-target image iS1 is the same drug shown in the reference image (master image iM1) (both showing the drug A)", and adds the collation-target image iS1 to a listing table for the drug A. Note that the processor 10 (drug collating unit 10C, listing-table creating unit 10F) creates the listing table for each kind of drugs.

In the meantime, it is determined that, as a result of collation, "the drug shown in the collation-target image iS1 is not the same drug shown in the reference image" (NO in step S150), the processor 10 (drug collating unit 10C) determines whether or not collation for all the collation-target images (with respect to a single reference image) is completed in step S170 (drug collating step). When it is determined to be affirmative (YES in step S170), the process shifts to step S180. When it is determined to be negative (NO in step S170), the process returns to step S130 to obtain a next collation-target image and perform collation (step S140: drug collating step).

In step S180, it is determined whether or not collation is completed for all the drugs listed in the prescription (all the drugs to be packaged in the packaging bag TP), and the process of step S120 to S170 (drug collating step, listing-table creating step) is repeated until it is determined to be affirmative. When it is determined to be affirmative (YES in step S180), the process shifts to step S190. In step S190, the processor 10 (drug collating unit 10C, listing-table creating unit 10F) determines whether or not the processes are completed for all the packaging bags TP included in the strip package PB. The processor 10 repeats the process of step S110 to S180 (drug collating step, listing table creating step) until it is determined to be affirmative in step S190, and then creates listing tables. When there are drugs different from any of the drugs listed in the prescription among the drugs included in the packaging bags, a list of such drugs may be created separately from the listing tables.

<Display of Listing Table>

The processor 10 (display control unit 10G) displays the listing table generated before step S190 for a single kind of drug among the drugs listed in the prescription on a display screen of the monitor 32 (step S200: display control step). Hereinafter, examples of display of the listing table are to be described.

(Display Example 1)

FIG. 9 is a diagram showing an example of a listing table L1 (listing table) for the drug A. In Display Example 1, the reference image (master image in this case) and the attribute information (information showing the attribute of the drug) regarding the drug A are displayed on the left side (regions L1A and L1B) of the listing table L1, respectively, and all of the collation-target images identified to be "showing the drug A" are displayed on the right side (region L1C). While only the image (for example, the collation-target image iS1 described above) of the front surface (surface where a mark is impressed) of the drug is included in the listing table L1 in FIG. 9, the image of the back surface (for example, the collation-target image iS2 described above) of the drug may also be included (see FIG. 16 of Display Example 7). In the region L1C of the listing table L1, collation targets are displayed for each packaging bag and for each dosing timing. In addition, inspection assisting information (information for efficiently collate and inspect the drugs) related to the packaging bags TP is also displayed along with the collation-target images. While the dosing timing, packaging bag number, dosing day are included in the inspection assisting information in the example of FIG. 9, other information (similarity between the reference image and the collation-target image, and the like) may also be included. Note that it is assumed in Display Example 1 that two tablets of drug A are properly packaged in all of the packaging bags and that the dosing period is 7 days (3 doses in a day×7 days=21 packaging bags).

On the listing table L1, the reference image and the collation-target images are displayed with their sizes and facing directions matched each other, after magnification or reduction and rotation by the processor 10 (listing-table creating unit 10F). In a lower region L1D, displayed are a button B1 for displaying a listing table of a previous drug (drug D in this case), a button B2 for displaying a listing table of a next drug (drug B in this case), and a button B3 for shifting to a menu screen for setting display conditions and the like. The user can operate those buttons B1 to B3 with operations via the operation unit 40. Note that it is possible to configure the system such that the user may select in advance, the drug for which the listing table is created and displayed (see FIG. 22 to be described later). The processor 10 (drug selecting unit 10D) receives selection of the drug (command for displaying the listing table) via button operation and/or operation on the drug selection screen, and the processor 10 (display control unit 10G) displays the listing table of the drug for which the selection is received. Note that same regions and buttons are provided also in other display examples to be described hereinafter (reference signs and explanations are omitted.)

According to Display Example 1, the monitor 32 displays on a single display screen, the listing table L1 (listing table) including: the reference image; all of the collation-target images determined to "show the same drug (drug A) as the drug shown by the reference image"; and inspection assisting information regarding the drug A as a single kind. Therefore, it is unnecessary to scroll the screen even when there are a large number of packaging bags (when there are a large number of drugs), so that the user (pharmacist) can perform drug inspection work efficiently. Further, according to Display Example 1, the listing table L1 for a single kind (drug A) is displayed on a single display screen of the display device, so that mistakenly collated drugs can be easily found. Therefore, the pharmacist (user) can perform drug inspection efficiently. Note that the listing table L1 can be displayed on a single screen by reducing the images of the drugs, setting the resolution of display to be equal to or less than the resolution of the display screen as necessary, for example.

(Display Example 2)

FIG. 10 shows a listing table L2 (listing table) where the dosing period of the drug A that is a single kind of drug, is 14 days. Because the dosing period is longer and the number of collation-target images are larger than those of Display Example 1, the processor 10 (listing-table creating unit 10F) reduces the collation-target images in size to create the listing table L2, and the processor 10 (display control unit 10G) causes the monitor 32 to display the listing table L2 on a single display screen. As described, the listing table L2 is displayed on a single display screen in Display Example 2 as in the case of Display Example 1, so that it is unnecessary to scroll the screen even when there are a large number of packaging bags (when there are a large number of drugs). Therefore, the user (pharmacist) can perform drug inspection work efficiently.

(Display Example 3)

<Display of Differently Formatted Listing Table>

FIG. 11 shows a listing table L3 (listing table) for the drug A of a single kind in a case where the dosing period is 14 days as in the case of Display Example 2. Unlike the case of the listing tables L1 and L2, the processor 10 (listing-table creating unit 10F, display control unit 10G) causes the monitor 32 to display the dosing timings (after breakfast, after lunch, after dinner) in the vertical direction of a region L3C, and the dosing days (1st day to 7th day, 8th day to 14th day) in the lateral direction in the listing table L3 on a single display screen. As described above, it is possible to change the format of the listing table depending on the number of packaging bags, the number of drugs, the dosing period, and the like, in the drug inspection assisting apparatus 1. Thereby, it is unnecessary to scroll the screen even when there are a large number of packaging bags (when there are a large number of drugs), so that the user (pharmacist) can perform drug inspection work efficiently.

(Display Examples 4, 5)

<Change in Inspection Assisting information Amount Depending on Number of Collation-Target Images>

In a case where there are a large number of collation-target images included in the listing table, the listing table may be displayed on a single display screen by changing the amount of the inspection assisting information included in the listing table depending on the number of the collation-target images, instead of reducing the collation-target images inn size in the case of Display Example 2 (see FIG. 10). For example, on a listing table L4 (listing table; Display Example 4) shown in FIG. 12, the packaging bag numbers ("Bag No. 1" and the like) included in Display Examples 1 and 2 (see FIGS. 9 and 10) are omitted. Further, on a listing table L5 (listing table; Display Example 5) shown in FIG. 13, the dosing timings and days are omitted in addition to the packaging bag numbers. As described above, the amount of the inspection assisting information included in the listing table is changed depending on the number of the collation-target images (decreasing the amount of the inspection assisting information included in the listing table when there are a large number of the collating-target images). Thereby, it becomes easier to see the listing table (images of the drugs) even when there are a large number of packaging bags (even when there are a large number of drugs) so that the pharmacist can perform the drug inspection work efficiently.

<Display of Inspection Assisting Information According to Designation of Images>

Figure 13:
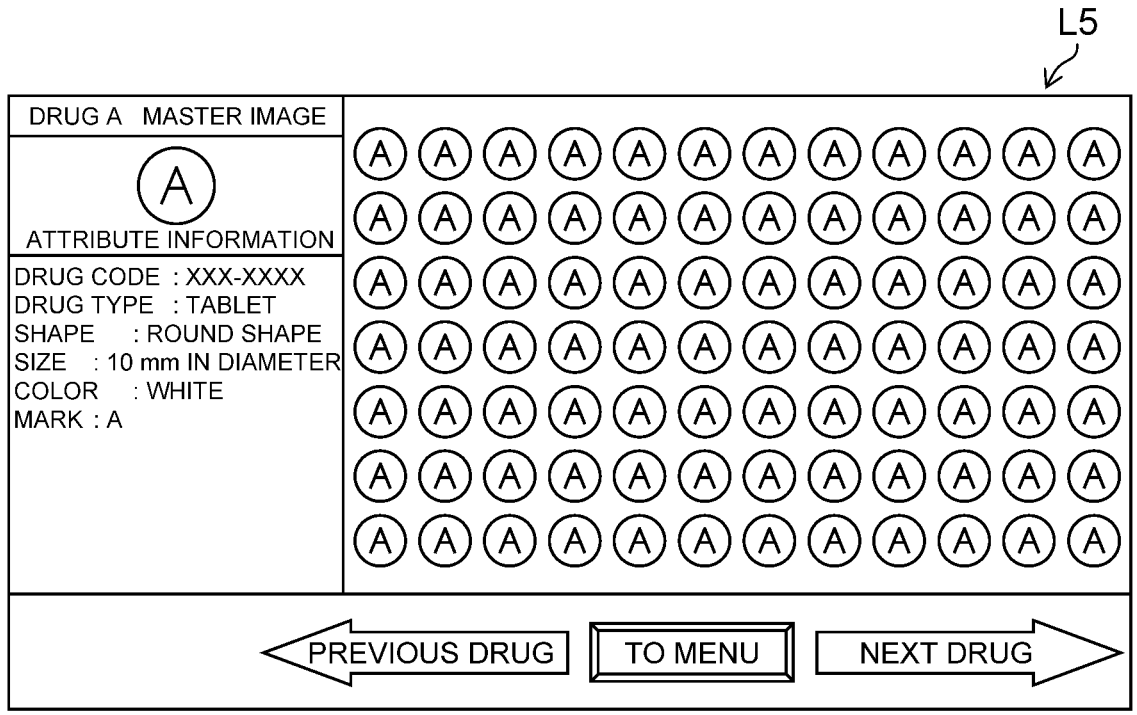
FIG. 13 is another diagram showing a state where the first listing table is displayed with inspection assisting information omitted.
Figure 14:
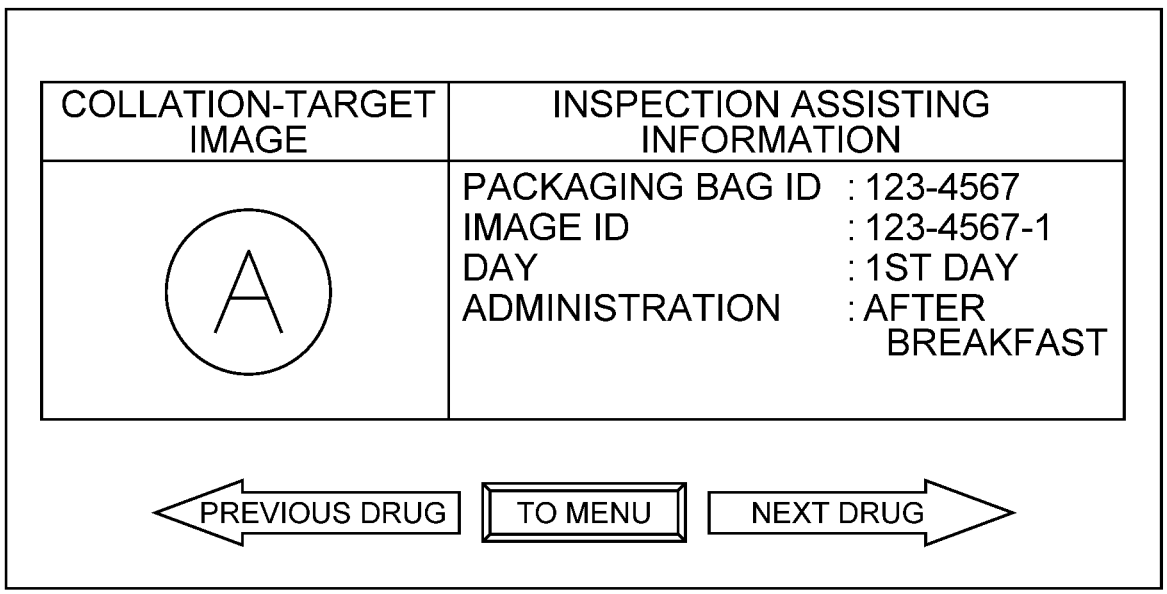
FIG. 14 is a diagram showing a display example of inspection assisting information.

While above Display Examples 4 and 5 describe aspects where "the amount of the inspection assisting information included in the listing table is decreased when there are a large number of collation-target images", there may still be a case where the user (pharmacist) desires to check the inspection assisting information even in such aspects. Thus, in the drug inspection assisting apparatus 1, the processor 10 stores in advance the collation-target images (collation-target images 20C) and the inspection assisting information (inspection assisting information 20G) in the storage unit 20 in an associated manner, and causes the monitor 32 to display the inspection assisting information regarding the designated image among the collation-target images included in the listing table. For example, when a collation-target image on the listing table L5 shown in FIG. 13 is designated (for example, clicked with a mouse of the operation unit 40), the processor 10 (display control unit 10G) displays the inspection assisting information such as the ID and the like of the packaging bag as shown in FIG. 14. Note that the inspection assisting information is not limited to the example of FIG. 14 but other information (for example, similarity between the reference image and the collation-target image) may be displayed. By displaying the inspection assisting information according to the designation of the collation-target image as described above, it is possible to easily check which image is determined to be "the same as the drug shown in the reference image" and the listing table is created therefor even when the inspection assisting information to be displayed on the listing table is decreased because there are a large number of packaging bags (number of drugs). Thereby, the user (pharmacist) can perform drug inspection work efficiently.

(Display Example 6)

<Display Example when There is Collation Error>

Figure 15:
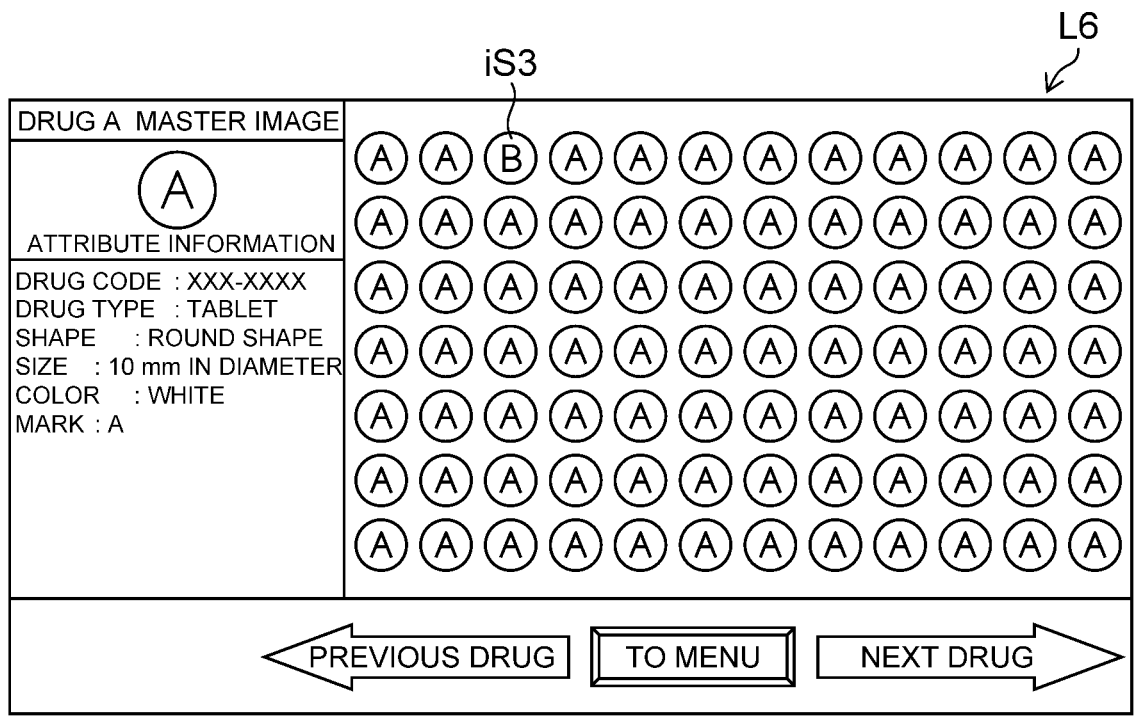
FIG. 15 is a diagram showing a state where a collation error is occurring.

FIG. 15 is a diagram showing an example of a listing table when there is a collation error. Because a listing table L6 shown in FIG. 15 is the listing table for the drug A, all of the collation-target images are supposed to be of the drug A if properly packaged. However, a collation-target image iS3 (drug B) of the third tablet is mistakenly determined as the drug A. Even in a case where there is such collation error, it is possible to easily grasp that there is a collation error by making a comparison with the master image, the reference image, or other collation-target images, so that the user (pharmacist) can perform the drug inspection work efficiently.

(Display Example 7)

<Display Example of Listing Table Including Image of Back Surface>

While Display Examples 1-6 mentioned above describe the case where the listing table includes the images (for example, the collation-target image iS1 of the drug A) of the front surface (face where the mark is impressed) of the drugs, the listing table may include the images (for example, the collation-target image iS2 of the drug A) of the back surface (face where the mark is not impressed) of the drugs. As in FIG. 16, for example, the listing table L6 (listing table for the drug B) may include images of the front surface and the images of the back surface for both the reference image and the collation-target images. As described, whether to include only the images of the front surface or to include the images of the front surface and back surface in the listing table may be determined by a user instruction made via the operation unit 40 or may be determined by the processor 10 (listing-table creating unit 10F, display control unit 10G) depending on whether or not the listing table can be fitted within a single display screen.

(Display Example 8)

While the listing table is displayed on a single display screen in Display Examples 1-7 mentioned above so that scrolling is unnecessary, it is also possible to provide a button Ma, a button Mb, and a slide bar Mc on the listing table as in a listing table L7 shown in FIG. 17, and the processor 10 (display control unit 10G) may scroll (move the periods to be displaced vertically) and display the listing table L7 according to the operation of the user. The listing table for a single kind of drug is also displayed with such display mode, so that the mistakenly collated drug can be easily found and the pharmacist (user) can perform the drug inspection efficiently. Further, the display region for the listing table can be expanded, so that the listing table can be displayed without performing reduction or the like on the images.

<Creation of Listing Table for Similar Drug>

Figures 22, 23A, 23B:
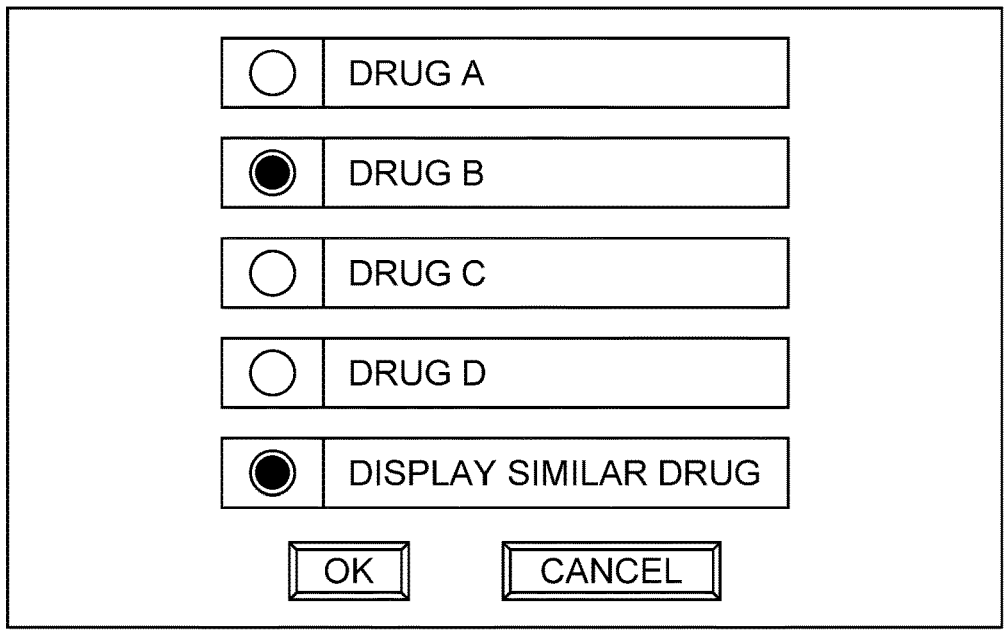
FIG. 22 is a diagram showing an example of a drug selection screen.
FIG. 23A is a diagram showing similarity relations among drugs.
FIG. 23B is a diagram showing similarity relations among drugs.

Below is explanation about processes performed by the drug inspection assisting apparatus 1 having the above configuration when a listing table for a similar drug is displayed in addition to the listing table for a single kind of drug. For example, the listing table for a similar drug may be displayed when the user clicks "display similar drug" at the time of inputting prescription information, in a case where the drug selection screen as shown in FIG. 22 is displayed. Or, for example, the listing table for a similar drug may be displayed by the drug inspection assisting apparatus 1 regardless of the operation of the user.

Figure 18:
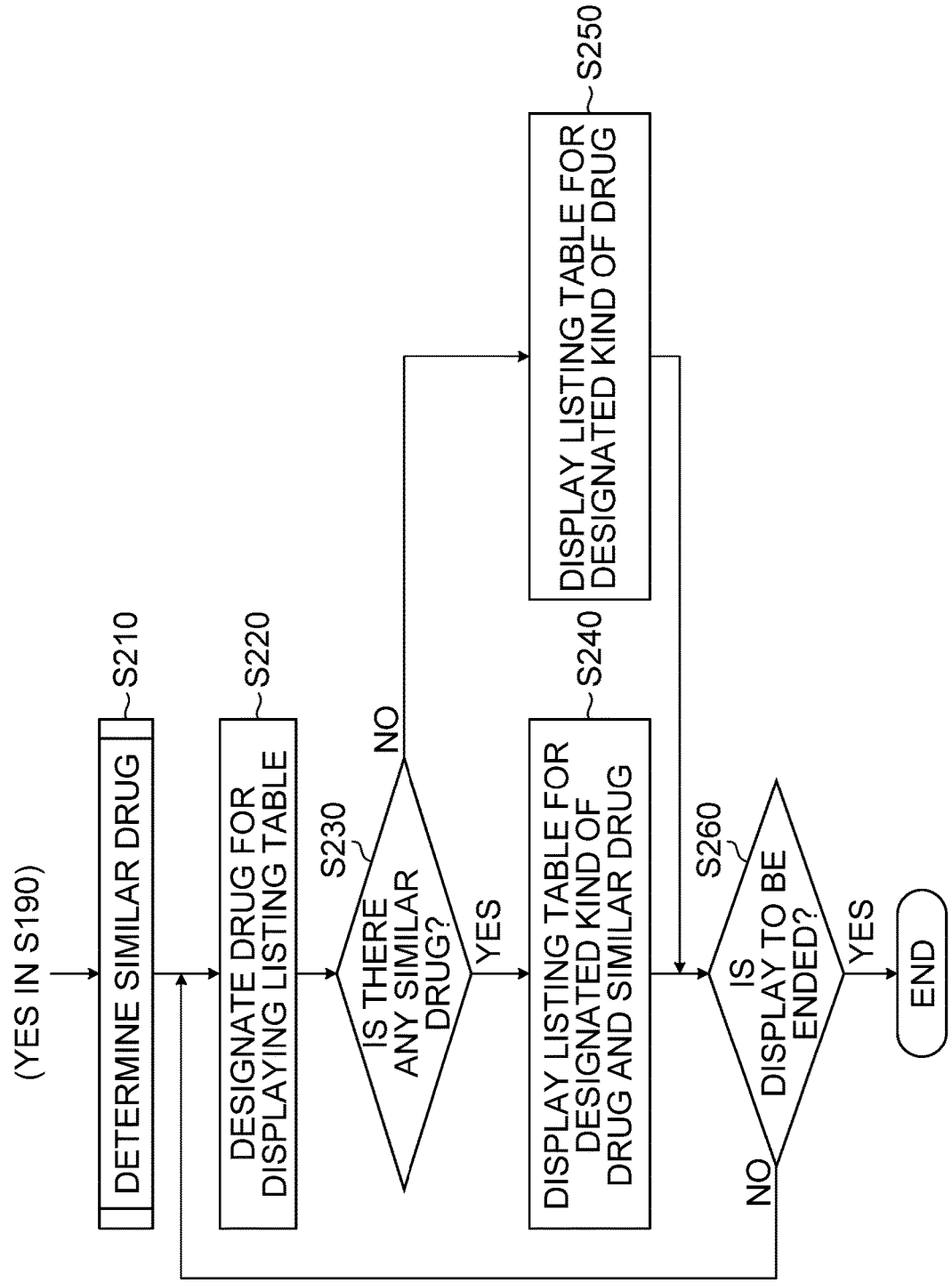
FIG. 18 is a flowchart showing processes performed when displaying a listing table for similar drugs.

FIG. 18 is a flowchart showing the processes performed when the listing table for the similar drug is displayed in addition to the listing table for a single kind of drug. Because the processes up to step S190 is the same as those in the flowchart shown in FIG. 6, FIG. 6 should be referred to for those processes. Those processes are not shown in FIG. 18 and detailed explanations thereof are omitted.

When it is determined to be affirmative in step S190 (collation is completed for all of the packaging bags), the processor 10 (drug collating unit 10C, similarity calculating unit 10E) determines a similar drug in step S210 (drug collating step, similarity calculating step). Detailed explanation about step S210 will be described later.

In step S220, the processor 10 designates the drug (a single kind of drug) for which the listing table is to be displayed. This designation may be performed by the drug selecting unit 10D according to a drug selecting operation by the user via the operation unit 40. Alternatively, the display control unit 10G may select one of the drugs (for example, the drug listed first) listed in the prescription to designate the drug for which the listing table is to be displayed. When the kind of drug to be displayed is designated, the processor 10 (display control unit 10G) determines whether or not there is a similar drug that is similar to the designated drug (step S230: display control step). When it is determined to be affirmative, the listing table for both the designated kind of drug and the similar drug is displayed on a single display screen of the monitor 32 (step S240: display control step). In the meantime, when it is determined to be negative in step S230, the listing table for the designated kind of drug is displayed on a single display screen of the monitor 32 (step S250: display control step). In step S260 (display control step), the processor 10 (display control unit 10G) determines whether or not to end display of the listing table. When there is an instruction to end (for example, when the user clicks an end button via the operation unit 40), it is determined to be affirmative in step S260 and the process is ended. In the meantime, when designated to display the listing table for another drug, it is determined to be negative in step S260 and the process returns to step S220. A display example of the listing table in step S240 will be described later (display in step S250 is display of the listing table for the designated kind of drug, so that it is the same as the case of Display Examples 1 to 8 described above).

Figure 19:
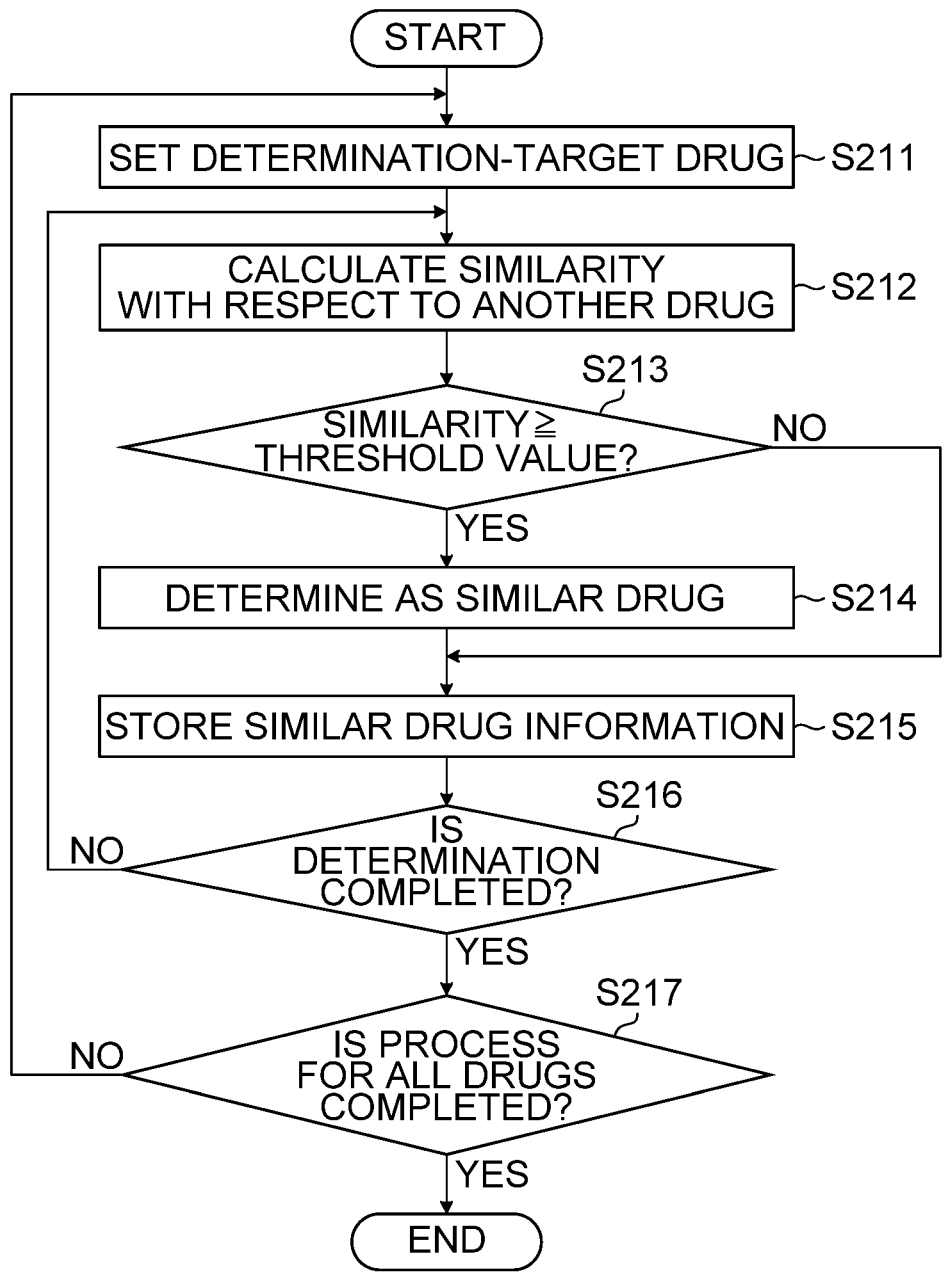
FIG. 19 is a flowchart showing similar drug determination process.

FIG. 19 is a flowchart showing the similar drug determination process in step S210 (drug collating step, similarity calculating step) of FIG. 18. The processor 10 (drug selecting unit 10D, similarity calculating unit 10E) sets a determination-target drug (step S211), and calculates the similarity between the set determination-target drug and another drug (step S212). For example, the drug A is set as the determination-target drug in step S211, and the similarity between the drug A and another drug B is calculated in step S212. In step S212, similarity between the master image of the drug A and the master image of the drug B can be calculated, for example. The processor 10 (similarity calculating unit 10E) determines whether or not the calculated similarity is equal to or more than a threshold value (step S213). When it is determined to be affirmative in step S213, the other drug is determined as a similar drug (step S214). In step S212, the similarity calculating unit 10E may calculate the similarity between the master image and the collation-target image or the similarity between the collation-target images, instead of calculating the similarity between the master images.

The processor 10 (similarity calculating unit 10E) stores the similarity (similarities) calculated in step S212 in the storage unit 20 as similar drug information 20E (step S215). The similar drug information 20E can be stored in a table format shown in FIG. 23A, for example. Further, it is also possible to apply a threshold value to the numerical values in the table and classify relations between the drugs to any one of "same, similar, dissimilar (non-similar)". FIG. 23B is a diagram showing a table when the threshold value of 0.8 is applied to the similarities shown in FIG. 23A, and the drug having the similarity of 1.0 is determined as "same", the drug having the similarity of 0.8 or more is determined as "similar", and the drug having the similarity of less than 0.8 is determined as "dissimilar (not similar)". In the example described above, the similarity between the drug A and the drug B is 0.6, so that both drugs are dissimilar drugs. Further, instead of the tables shown in FIG. 23A and FIG. 23B, or in addition to these Figures, the storage unit 20 may store a table including only information about the similar drugs for certain drugs as shown in FIG. 24. Further, instead of newly creating the tables shown in FIG. 23A to FIG. 24, the tables previously stored in the storage unit 20 may be updated (overwritten).

The processor 10 (drug selecting unit 10D, similarity calculating unit 10E) determines whether or not determination between the single determination-target drug and all of the other drugs (for example, between the drug A and the other drugs B, C, D) is completed (step S216). When it is determined to be affirmative, it is then determined whether or not determination for all of the drugs (drugs A to D) is completed (step S217), and the processes of steps S211 to S216 are repeated until it is determined to be affirmative. When it is determined to be affirmative in step S216, the process returns to the flowchart of FIG. 18 and shifts to step S220.

<Display Example of Listing Table>
(Display Example 9)

Figure 20A:
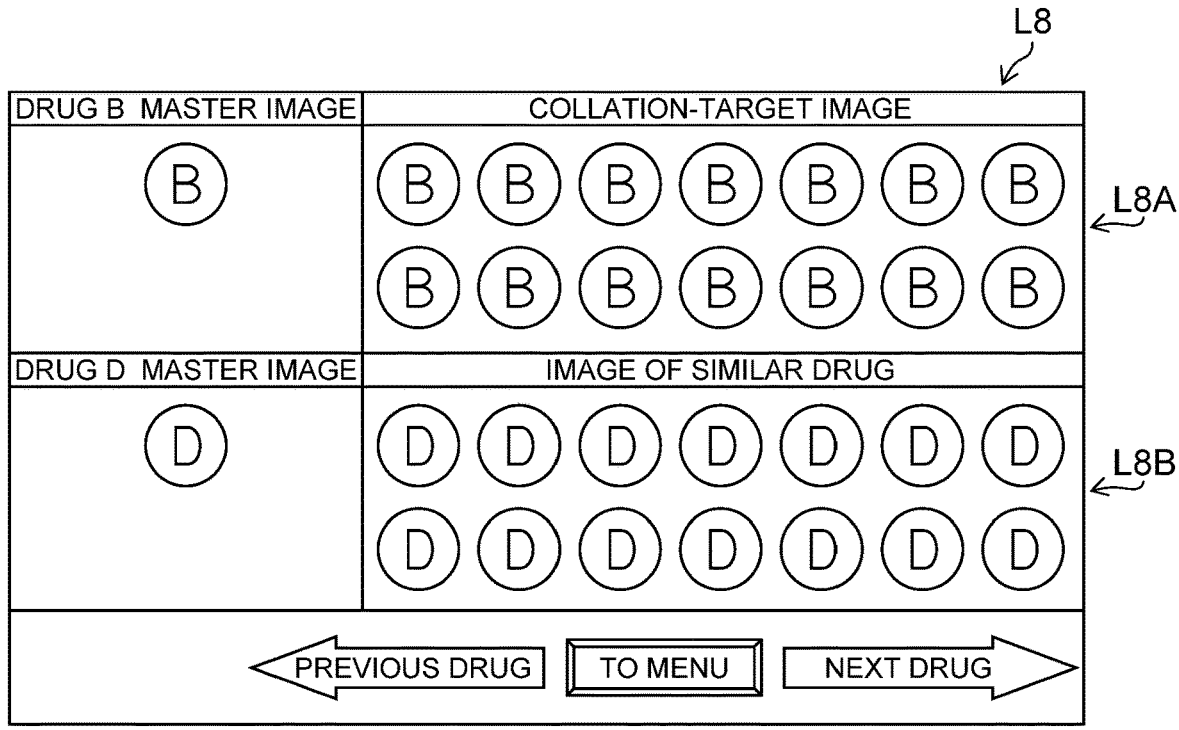
FIG. 20A is a diagram showing a state where a listing table for a designated drug and a similar drug is displayed.
Figure 20B:
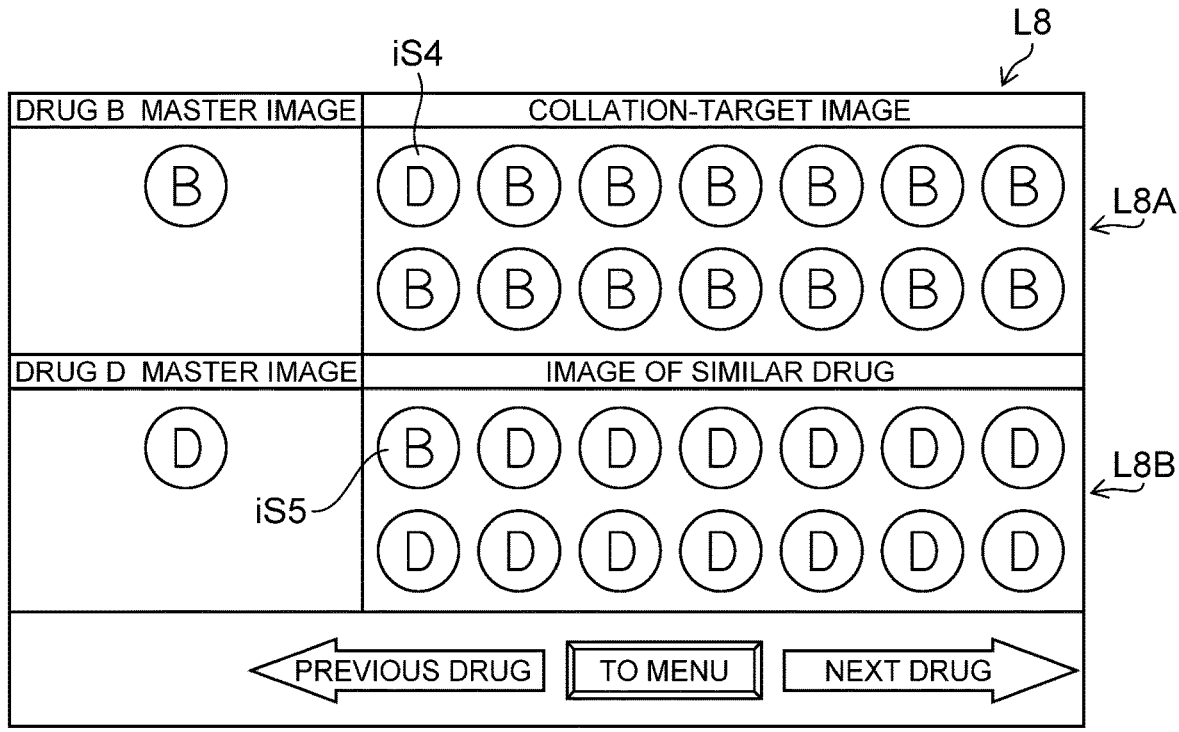
FIG. 20B is a diagram showing a state where a listing table for a designated drug and a similar drug is displayed.

A display example of a listing table in step S240 shown in FIG. 18 will be described. FIG. 20A and FIG. 20B are diagrams showing the display examples of the listing table for the designated drug and the similar drug. FIG. 20A shows a listing table L8 including a listing table L8A (listing table) for the drug B and a listing table L8B (listing table) for the drug D that is a similar drug of the drug B (see FIG. 23A to FIG. 24). Further, FIG. 20B shows a state where a drug collation error occurs in the listing table L8 (the drug D shown by a collation-target image iS4 is determined as the drug B in the listing table L8A and, inversely, the drug B shown by a collation-target image iS5 is determined as the drug D in the listing table L8B). Even when the similar drugs (the drug B and the drug D) are switched because of the collation error as described above, the user (pharmacist) can easily recognize the collation error through displaying the listing table L8B for the drug D as the similar drug along with the listing table L8A for the drug B. Further, the listing tables L8A and L8B are displayed on a single display screen so that it is unnecessary to scroll the screen even when there are a large number of drugs. Therefore, the user can perform the drug inspection work efficiently. Note that the listing table L8 can be displayed on a single screen by reducing size of the images of the drugs or setting the resolution of display to be equal to or less than the resolution of the display screen as necessary, for example.

Here, as in the case of displaying the listing table L1 shown in FIG. 9, for example, when the processor 10 (drug selecting unit 10D) receives selection of the drug (instruction for displaying a listing table) through an operation of the buttons (buttons B1, B2 in FIG. 9) and/or an operation on the drug selection screen (see FIG. 22), and the processor 10 (display control unit 10G) causes the monitor 32 to display the listing table for the drug for which the selection is received.

(Display Example 10)

Figure 21A:
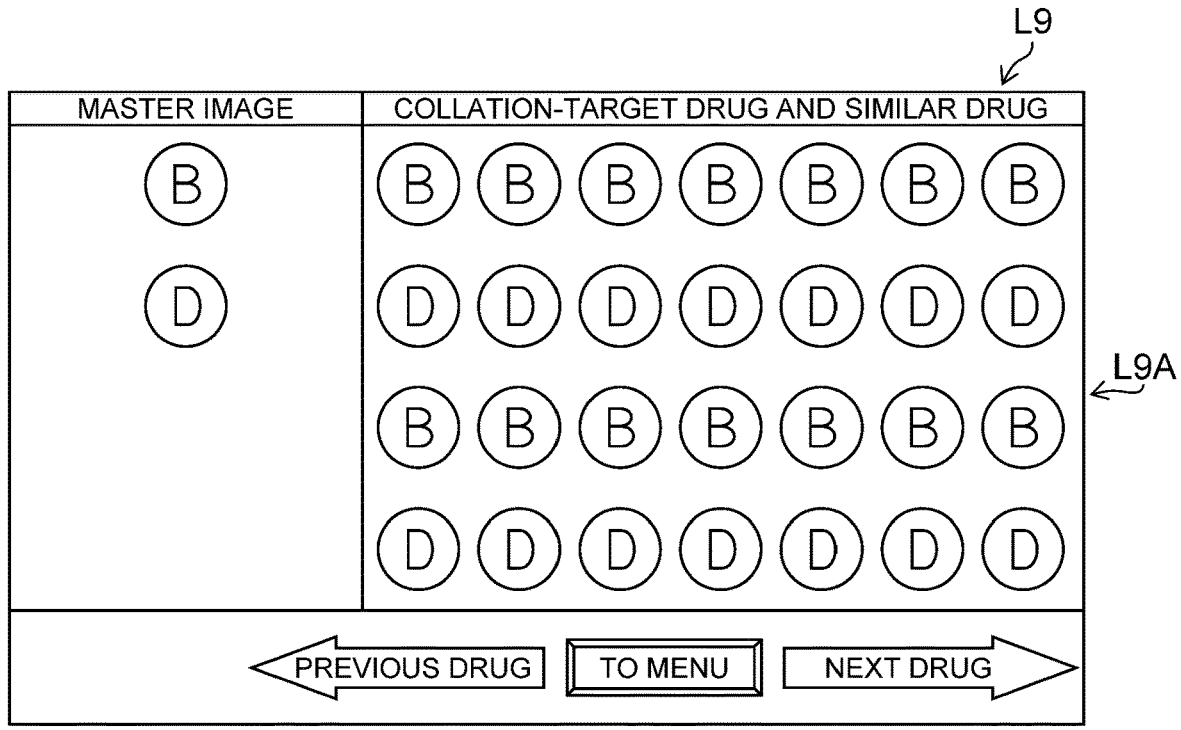
FIG. 21A is another diagram showing a state where a listing table for a designated drug and a similar drug is displayed.
Figure 21B:
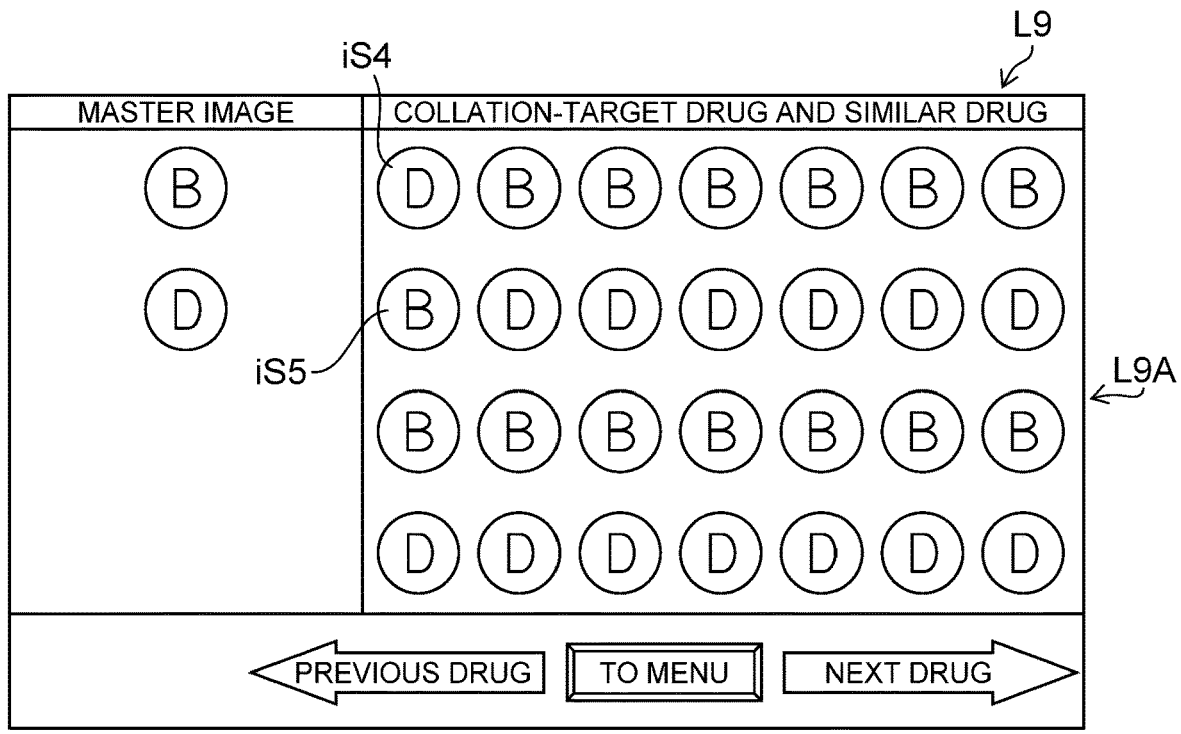
FIG. 21B is another diagram showing a state where a listing table for a designated drug and a similar drug is displayed.

FIGS. 21A and 21B are diagrams showing other display examples of the listing table for the designated drug and the similar drug. While FIG. 20A and FIG. 20B display the listing table L8A and the listing table L8B in the individual regions in the listing table L8, FIG. 21A and FIG. 21B display those listing tables in a single region (display on a single display screen of the monitor 32). Specifically, the image of the drug B and the image of the drug D (drugs included in a same packaging bag TP) are arranged vertically and displayed in the same region (in one region) L9A in a listing table L9 (listing table) as shown in FIG. 21A. Further, FIG. 21B shows a state where a collation error similar to that shown in FIG. 20B is occurring. With the display shown in FIG. 21A and FIG. 21B, the user (pharmacist) can also recognize the collation error easily and perform the drug inspection work efficiently. Note that the listing table L9 can also be displayed on a single display screen of the monitor 32 in the same manner as that of the listing table L8.

Figure 12:
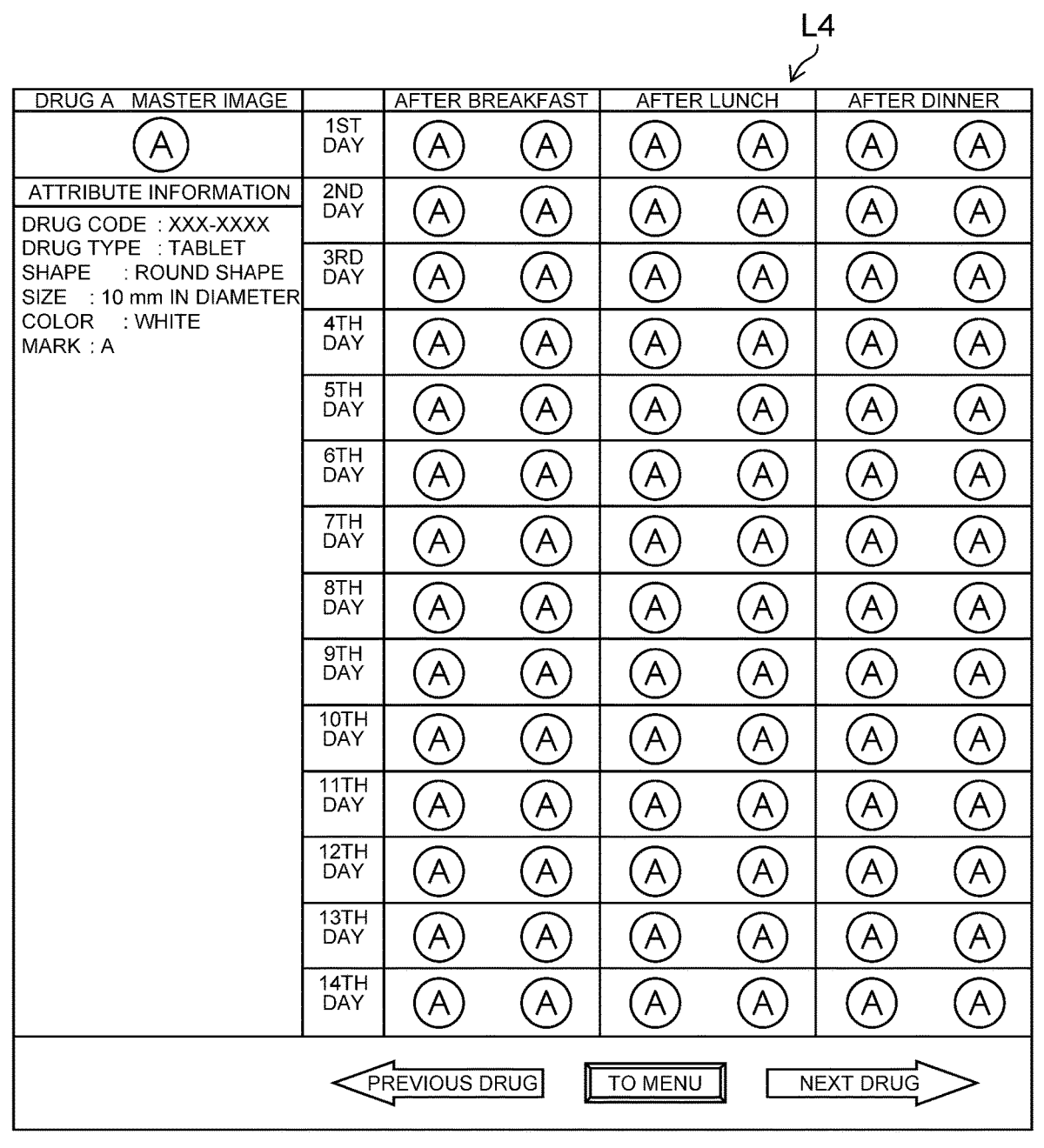

Also when displaying the listing table for the designated drug and the similar drug as shown in FIG. 20A to FIG. 21B, the images may be magnified or reduced in size depending on the number of collation-target images or the amount of the inspection assisting information included in the listing table may be changed depending on the number of collation-target images (for example, decrease the amount of the inspection assisting information when there are a large number of collation-target images as shown in FIG. 12 and FIG. 13). Further, as in the case of FIG. 14, the inspection assisting information may be displayed according to designation of the images to be included in the listing table. Through displaying the listing table in the manner described above, the listing table (images of the drugs) can be easily viewed even when there are a large number of packaging bags (when there are a large number of drugs) so that the pharmacist can perform the drug inspection work efficiently.

In a case of displaying the listing table for the designated drug and the similar drug as in FIG. 20A to FIG. 21B, the listing table may also be scrolled (the period to be displayed may be vertically moved) and displayed in the same manner as described in FIG. 17. Because the listing table for a single kind of drug is displayed even in such display mode, a mistakenly collated drug may be easily found and the pharmacist (user) can perform the drug inspection work efficiently. Further, because the display region of the listing table can be expanded, the listing table can be displayed without size-reduction or the like of the images.

While an embodiment and examples of the present invention have been described above, the present invention is not limited to the aspects described above and various modifications are possible without departing from the spirit and scope of the present invention.

REFERENCE SIGNS LIST

1: Drug inspection assisting apparatus
10: Processor
10A: Prescription input unit
10B: Imaging unit
10C: Drug collating unit
10D: Drug selecting unit
10E: Similarity calculating unit
10F: Listing-table creating unit
10G: Display control unit
10H: Communication unit
12: Lighting unit
13: Light source
15A: Camera
15B: Camera
16: Prescription reader
20: Storage unit
20A: Prescription information
20B: Reference image
20C: Collation-target image
20D: Attribute information
20E: Similar drug information
20F: Listing table
20G: Inspection assisting information
30: Display unit
32: Monitor
40: Operation unit
50: Conveying mechanism
A: Drug
B: Drug
B1: Button
B2: Button
B3: Button
C: Drug
D: Drug
L1: Listing table
L1A: Region
L1B: Region
L1C: Region
L1D: Region
L2: Listing table
L3: Listing table
L3C: Region
L4: Listing table
L5: Listing table
L6: Listing table
L7: Listing table
L7A: Listing table
L7B: Listing table
L8: Listing table
L8A: Listing table
L8B: Listing table
L9: Listing table
L9A: Region
PA: Imaging optical axis
PB: Strip package
S100 to S260: Each step of drug inspection assisting method
TP: Packaging bag
iM1: Master image
iM2: Master image
iS1: Collation-target image
iS2: Collation-target image
iS3: Collation-target image
iS4: Collation-target image
iS5: Collation-target image

What is claimed is:

1. A drug inspection assisting apparatus for inspecting drugs dispensed and packaged in a packaging bag according to a prescription, the drug inspection assisting apparatus comprising a processor, wherein the processor performs:
collating a reference image of each drug listed in the prescription and a collation-target image based on a captured image of drugs packaged in the packaging bag and determining whether or not the drug shown by the collation-target image and the drug shown by the reference image are the same drug;
creating, for each kind of the drugs to be packaged in the packaging bag, a listing table including the reference image of drug to be dispensed according to the prescription and all images which are determined to show the same drug as the drug shown by the reference image, among collation-target images; and causing a display device to display the listing table for a single kind of drug among kinds of the drugs listed in the prescription on a display screen.

2. The drug inspection assisting apparatus according to claim 1, wherein the processor further causes the display device to display the listing table for a similar drug which is similar to the single kind of drug on the display screen.

3. The drug inspection assisting apparatus according to claim 2, wherein the processor further calculates similarity between the drugs,
and determines that a drug whose calculated similarity to the single kind of drug is equal to or more than a threshold value as the similar drug, and causes the display device to display the listing table for the similar drug.

4. The drug inspection assisting apparatus according to claim 2, wherein the processor further causes the display device to display, according to an instruction to display a designated kind of drug, the listing table for the designated kind of drug and the similar drug on the display screen.

5. The drug inspection assisting apparatus according to claim 1, wherein the processor further
creates the listing table including inspection assisting information of the collation-target images, and
causes the display device to display the listing table including the inspection assisting information on the display screen.

6. The drug inspection assisting apparatus according to claim 5, wherein the processor further changes an amount of the inspection assisting information to be included in the listing table depending on a number of the collation-target images included in the listing table.

7. The drug inspection assisting apparatus according to claim 5, wherein the processor further causes the display device to display the inspection assisting information regarding only a designated image among the collation-target images displayed on the display screen.

8. The drug inspection assisting apparatus according to claim 1, wherein:
the reference image includes a plurality of images obtained by imaging each of the drugs to be dispensed according to the prescription from a plurality of directions; and
the processor further creates the listing table including the plurality of images.

9. The drug inspection assisting apparatus according to claim 1, wherein the processor further performs imaging the packaged drugs from a plurality of directions to obtain a plurality of captured images, and
creates the listing table including a plurality of collation-target images respectively corresponding to the plurality of the captured images.

10. The drug inspection assisting apparatus according to claim 1, wherein the processor further creates the listing table with a size of the collation-target image adjusted to the reference image by magnifying or reducing the collation-target image.

11. The drug inspection assisting apparatus according to claim 1, wherein the processor further creates the listing table with a direction of the collation-target image adjusted to the reference image by rotating the collation-target image.

12. The drug inspection assisting apparatus according to claim 1, wherein the reference image is a master image stored in advance for each drug possible to be dispensed or a processed master image obtained by performing image-processing on the master image.

13. The drug inspection assisting apparatus according to claim 1, wherein the collation-target image is the captured image or a processed captured image obtained by performing image-processing on the captured image.

14. The drug inspection assisting apparatus according to claim 13, wherein the image-processing is an image-processing for extracting a drug region from the captured image.

15. The drug inspection assisting apparatus according to claim 1, wherein the processor further receives selection of a drug from a user, and
causes the display device to display the listing table for the drug for which the selection is received.

16. The drug inspection assisting apparatus according to claim 1, wherein the processor further causes the display device to display the listing table on a single display screen.

17. A drug inspection assisting method for inspecting drugs dispensed and packaged in packaging bag according to a prescription by a drug inspection assisting apparatus, the drug inspection assisting method comprising:
by the drug inspection assisting apparatus, performing a drug collating step of collating a reference image of each drug listed in the prescription and a collation-target image based on a captured image of drugs packaged in the packaging bag to determine whether or not the drug shown by the collation-target image and the drug shown by the reference image are the same drug;
by the drug inspection assisting apparatus, performing a listing-table creating step of creating, for each kind of the drugs to be packaged in the packaging bag, a listing table including the reference image of drug to be dispensed according to the prescription and all images which are determined to show the same drug as the drug shown by the reference image, among collation-target images; and
by the drug inspection assisting apparatus, performing a display control step of causing a display device to display the listing table for a single kind of drug among kinds of the drugs listed in the prescription on a display screen.

18. The drug inspection assisting method according to claim 17, wherein, by the drug inspection assisting apparatus, the display device is caused to display the listing table for a similar drug which is similar to the single kind of drug on the display screen in the display control step.

19. The drug inspection assisting method according to claim 18, further comprising
by the drug inspection assisting apparatus, performing a similarity calculating step of calculating similarity between drugs; and
by the drug inspection assisting apparatus, it is determined that a drug whose calculated similarity to the single kind of drug is equal to or more than a threshold value as the similar drug, and the display device is caused to display the listing table for the similar drug.

20. The drug inspection assisting method according to claim 18, wherein, in the display control step, according to an instruction to display a designated kind, the listing table for the designated kind of drug and the similar drug is displayed on the display screen.

21. The drug inspection assisting method according to claim 17, wherein, in the display control step, the listing table is displayed on a single display screen of the display device.

* * * * *